(12) United States Patent
Molnar et al.

(10) Patent No.: US 9,404,140 B1
(45) Date of Patent: Aug. 2, 2016

(54) PATTERNED CARDIOMYOCYTE CULTURE ON MICROELECTRODE ARRAY

(75) Inventors: Peter Molnar, Szombathely (HU); Anupama Natarajan, Chennai (IN); Maria Stancescu, Oviedo, FL (US); James Hickman, Orlando, FL (US)

(73) Assignee: The University of Central Florida Research Foundation, Inc., Orlando, FL (US)

( * ) Notice: Subject to any disclaimer, the term of this patent is extended or adjusted under 35 U.S.C. 154(b) by 942 days.

(21) Appl. No.: 12/938,701

(22) Filed: Nov. 3, 2010

Related U.S. Application Data

(60) Provisional application No. 61/257,504, filed on Nov. 3, 2009.

(51) Int. Cl.
*C12Q 1/02* (2006.01)
*C12Q 1/04* (2006.01)
*G01N 33/50* (2006.01)

(52) U.S. Cl.
CPC .............. *C12Q 1/04* (2013.01); *G01N 33/5008* (2013.01); *C12Q 1/02* (2013.01)

(58) Field of Classification Search
None
See application file for complete search history.

(56) References Cited

U.S. PATENT DOCUMENTS

| | | | |
|---|---|---|---|
| 5,422,510 A | 6/1995 | Schwartz | 364/452 |
| 5,682,899 A | 11/1997 | Nashef et al. | |
| 5,948,621 A | 9/1999 | Turner | 435/6 |
| 6,866,383 B2 | 3/2005 | Naik | 347/105 |
| 6,916,541 B2 | 7/2005 | Pantano | 428/429 |
| 6,935,165 B2 | 8/2005 | Bashir | 73/64.53 |
| 7,384,786 B2 * | 6/2008 | Freyman et al. | 435/395 |
| 7,541,146 B2 | 6/2009 | Lewis | 435/6 |
| 7,579,189 B2 * | 8/2009 | Freyman et al. | 435/395 |
| 7,691,629 B2 | 4/2010 | Johe | 435/402 |
| 7,860,563 B2 | 12/2010 | Foreman et al. | |
| 7,923,015 B2 | 4/2011 | Vazquez-Martinez | 424/192.1 |
| 7,927,671 B2 | 4/2011 | Kato | 428/1.1 |
| 8,071,319 B2 | 12/2011 | Metzger | 435/7.2 |
| 8,178,629 B2 | 5/2012 | Mao | 524/109 |
| 8,318,488 B1 * | 11/2012 | Bohlen et al. | 435/375 |
| 8,318,489 B2 * | 11/2012 | Davidson et al. | 435/377 |
| 8,318,951 B2 * | 11/2012 | Olson et al. | 548/365.7 |
| 8,828,721 B1 | 9/2014 | Hickman et al. | |
| 2003/0065452 A1 | 4/2003 | Hickman | 435/29 |
| 2003/0144823 A1 | 7/2003 | Fox | 703/11 |
| 2003/0211542 A1 | 11/2003 | Lee | 435/7.1 |
| 2005/0074834 A1 | 4/2005 | Chaplen et al. | |
| 2006/0105457 A1 | 5/2006 | Rameshwar | 435/368 |
| 2006/0259992 A1 | 11/2006 | Koren et al. | |
| 2007/0015138 A1 | 1/2007 | Barlow | 435/4 |
| 2007/0089515 A1 | 4/2007 | Shih et al. | |
| 2007/0117217 A1 | 5/2007 | Lal | 436/513 |
| 2007/0122896 A1 | 5/2007 | Shuler et al. | |
| 2007/0129447 A1 | 6/2007 | Sra | |
| 2007/0212723 A1 * | 9/2007 | Dudley et al. | 435/6 |
| 2008/0124789 A1 | 5/2008 | Hickman | 702/19 |
| 2008/0227137 A1 | 9/2008 | Zhang | 435/366 |
| 2009/0029463 A1 | 1/2009 | Collins | 435/366 |
| 2009/0227469 A1 | 9/2009 | Conklin et al. | |
| 2009/0239940 A1 * | 9/2009 | Del Monte et al. | 514/44 R |
| 2009/0305319 A1 | 12/2009 | Baudenbacher | 436/34 |
| 2011/0250682 A1 | 10/2011 | Hickman | 435/176 |
| 2012/0122728 A1 | 5/2012 | Hickman | 435/6 |
| 2012/0128639 A1 | 5/2012 | Hickman | 435/525 |
| 2013/0096888 A1 | 4/2013 | Hickman | 703/11 |
| 2013/0115694 A1 | 5/2013 | Hickman | 435/347 |
| 2014/0274796 A1 | 9/2014 | Hickman | |
| 2015/0219622 A1 | 8/2015 | Hickman | |

FOREIGN PATENT DOCUMENTS

| | | |
|---|---|---|
| CA | 2788905 | 2/2011 |
| CA | 2798777 | 5/2011 |
| EP | 2434896 | 4/2012 |
| EP | 2435585 | 4/2012 |
| EP | 2531910 | 12/2012 |
| EP | 2585171 | 5/2013 |
| WO | 2001/029206 | 4/2001 |
| WO | 2005/033264 | 4/2005 |
| WO | 2005/108598 | 11/2005 |

(Continued)

OTHER PUBLICATIONS

Badie et al., Novel Micropatterned Cardiac Cell Cultures with Realistic Ventricular Microstructure, Biophysical Journal, vol. 96, May 2009, pp. 3873-3885.*
Kim et al., Micropatterning of Cardiomyocytes using Adhesion-resistant Polymeric Microstructures, IEEE, 2005.*
Dhir, Application of Polyelectrolyte Multilayers for Photolithographic Patterning of Diverse Mammalian Cell Types in Serum Free Medium, MS Thesis, Fall 2008.*
U.S. Appl. No. 12/117,339, filed May 8, 2008, J. Hickman.
U.S. Appl. No. 12/145,810, filed Jun. 25, 2008, J. Hickman.
U.S. Appl. No. 12/661,323, filed Mar. 15, 2010.

(Continued)

*Primary Examiner* — Taeyoon Kim
*Assistant Examiner* — Srikanth Patury
(74) *Attorney, Agent, or Firm* — Meunier Carlin & Curfman LLC

(57) ABSTRACT

The invention provides a culture of patterned cardiomyocytes, the culture including a support substrate bearing a multielectrode array, a negative surface resistant to cell attachment and deposited on the support substrate covering the multi-electrode array, a pattern ablated on the negative surface, a positive surface promoting cell attachment deposited on the pattern ablated on the negative surface; and cardiomyocytes adherent to the positive surface and growing aligned along the pattern ablated on the negative surface. The invention also includes a method of making the culture of patterned cardiomyocytes and a method of in vitro method of testing the effect of a compound on cardiac function by measuring electrical output from the patterned cardiomyocytes.

8 Claims, 6 Drawing Sheets

(56) References Cited

FOREIGN PATENT DOCUMENTS

| | | |
|---|---|---|
| WO | 2009/036573 | 3/2009 |
| WO | 20090036573 | 3/2009 |
| WO | 20100127280 | 11/2010 |
| WO | 20100138679 | 12/2010 |
| WO | WO 2010/138679 | 12/2010 |
| WO | WO 2010/138782 | 12/2010 |
| WO | WO 2011/097574 | 8/2011 |
| WO | WO 2011/133985 | 10/2011 |
| WO | WO 2012/158923 | 11/2012 |
| WO | 2013/013206 | 1/2013 |
| WO | 2014/028940 | 2/2014 |
| WO | 2014/120952 | 8/2014 |

OTHER PUBLICATIONS

U.S. Appl. No. 12/465, 399, filed Apr. 22,2010, J. Hickman.
U.S. Appl. No. 12/788,732, filed May 27, 2010, J. Hickman.
U.S. Appl. No. 12/938,701, filed Nov. 3, 2010, J. Hickman.
U.S. Appl. No. 13/102,672, filed May 6, 2011, J. HIckman.
U.S. Appl. No. 60/916,641, filed May 8, 2007, J. Hickman.
U.S. Appl. No. 60/945,952, filed Jun. 25, 2007, J. Hickman.
U.S. Appl. No. 61/159,851, filed Mar. 19, 2009, J. Hickman.
U.S. Appl. No. 61/171,958, filed Apr. 23, 2009, J. Hickman.
U.S. Appl. No. 61/171,968, filed Apr. 23, 2009, J. Hickman.
U.S. Appl. No. 61/181,718, filed May 28, 2009, J. Hickman.
U.S. Appl. No. 61/181,737, filed May 28, 2009, J. Hickman.
U.S. Appl. No. 61,181,868, filed May 28, 2009, J. Hickman.
U.S. Appl. No. 61/252,195, filed Oct. 16, 2009, J. Hickman.
U.S. Appl. No. 61/257,504, filed Nov. 3, 2009, J. Hickman.
U.S. Appl. No. 61/259,715, filed Nov. 10, 2009, J. Hickman.
U.S. Appl. No. 61,301,669, filed Feb. 5, 2010, J. Hickman.
U.S. Appl. No. 61/331,999, filed May 6, 2010, J. Hickman.
U.S. Appl. No. 61/332,003, filed May 6, 2010, J. Hickman.
U.S. Appl. No. 61/487,251, filed May 17, 2011, J. Hickman.
U.S. Appl. No. 61/684,168, filed Aug. 17, 2012, J. Hickman.
U.S. Appl. No. 61/732,042, filed Nov . 30, 2012, J. Hickman.
U.S. Appl. No. 61/732,574, filed Dec. 3, 2012, H, Hickman.
U.S. Appl. No. 61/758,623, filed Jan. 30, 2013, J. Hickman.
U.S. Appl. No. 61/784,923, filed Mar. 14, 2013, J. Hickman.
U.S. Appl. No. 61/789,184, filed Mar. 15, 2013, J. Hickman.
U.S. Appl. No. 61/789,587, filed Mar. 15, 2013, J. Hickman.
U.S. Appl. No. 61/790,061, filed Mar. 15, 2013, J. Hickman.
Preliminary Amendment filed Jul. 10, 2012 for U.S. Appl. No. 12/117,339, filed May 8, 2008 (Hickman et al—inventors)(5 pages).
Non-Final Office Action issued Aug. 24, 2012 for U.S. Appl. No. 12/117,339, filed May 8, 2008 (Hickman et al—inventors)(10 pages).
Response to Non-Final Office Action filed Jan. 24, 2013 for U.S. Appl. No. 12/117,339, filed May 8, 2008 (Hickman et al—inventors)(8 pages).
Restriction Requirement issued Jun. 7, 2011 for U.S. Appl. No. 12/145,810, filed Jun. 25, 2008 (Hickman et al—inventors)(5 pages).
Response to Restriction Requirement filed Jul. 5, 2011 for U.S. Appl. No. 12/145,810, filed Jun. 25, 2008 (Hickman et al—inventors)(7 pages).
Non-Final Office Action issued Aug. 31, 2011 for U.S. Appl. No. 12/145,810, filed Jun. 25, 2008 (Hickman et al—inventors)(8 pgs.).
Response to Non-Final Office Action filed Jan. 31, 2012 for U.S. Appl. No. 12/145,810, filed Jun. 25, 2008 (Hickman et al—nventors)(13 pages).
Final Office Action issued Apr. 9, 2012 for U.S. Appl. No. 12/145,810, filed Jun. 25, 2008 (Hickman et al—inventors)(7 pages).
Notice of Abandonment issued on Oct. 19, 2012 for U.S. Appl. No. 12/145,810, filed Jun. 25, 2008 (Hickman et al—inventors)(2 pages).
Restriction Requirement issued Sep. 27, 2012 for U.S. Appl. No. 12/661,323, filed Mar. 15, 2010 (Hickman et al—inventors)(10 pages).
Response to Restriction Requirement filed Nov. 17, 2012 for U.S. Appl. No. 12/661,323, filed Mar. 15, 2010 (Hickman et al—inventors)(7 pages).
Non-Final Office Action issued Mar. 13, 2013 for for U.S. Appl. No. 12/661,323, filed Mar. 15, 2010 (Hickman et al—inventors)(14 pages).
Response to Non-Final Office Action filed Jul. 12, 2013 for U.S. Appl. No. 12/661,323, filed Mar. 15, 2010 (Hickman et al—inventors)(11 pages).
Restriction Requirement issued Aug. 7, 2012 for U.S. Appl. No. 12/765,996, filed Feb. 23, 2010 (Hickman et al—inventors)(6 pages).
Response to Restriction Requirement filed on Sep. 7, 2012 for U.S. Appl. No. 12/765,996, filed Feb. 23, 2010 (Hickman et al—inventors)(7 pages).
Non-Final Office Action issued Nov. 13, 2012 for U.S. Appl. No. 12/765,996, filed Feb. 23, 2010 (Hickman et al—inventors)(11 pages).
Response to Non-Final Office Action filed on Apr. 12, 2013 for U.S. Appl. No. 12/765,996, filed Feb. 23, 2010 (Hickman et al—inventors)(70 pages).
Notice of Non-Compliant Amendment issued Apr. 19, 2013 for U.S. Appl. No. 12/765,996, filed Feb. 23, 2010 (Hickman et al—inventors)(2 pages).
Letter Withdrawing a Notice of Non-Compliant Amendment issued Apr. 25, 2013 for U.S. Appl. No. 12/765,996, filed Feb. 23, 2010 (Hickman et al—inventors)(2 pages).
Restriction Requirement issued Oct. 3, 2012 for U.S. Appl. 13/102,672, filed May 6, 2011 (Hickman et al—inventors)(7 pages).
Response to Restriction Requirement filed Nov. 16, 2012 for U.S. Appl. 13/102,672, filed May 6, 2011 (Hickman et al—inventors)(6 pages).
Preliminary Amendment filed Nov. 6, 2012 for U.S. Appl. No. 13/696,396, filed Nov. 6, 2012 (Hickman, et al—inventors)(4 pages).
Restriction Requirement issued Sep. 30, 2013 for U.S. Appl. No. 13/696,396, filed Nov. 6, 2012 (Hickman, et al—inventors)(11 pages).
International Search Report issued Jul. 28, 2011 for PCT Application No. PCT/US2011/035585, which published as WO 2011/133985 on Oct. 27, 2011 (Applicant: University of Central Florida Research Foundation // Inventors—James Hickman, et al)(2 Pages).
Written Opinion issued Jul. 28, 2011 for PCT Application No. PCT/US2011/035585, which published as WO 2011/133985 on Oct. 27, 2011 (Applicant: University of Central Florida Research Foundation // Inventors—James Hickman, et al)(4 pages).
International Preliminary Report on Patentability issued Oct. 23, 2012 for for PCT Application No. PCT/US2011/035585, which published as WO 2011/133985 on Oct. 27, 2011 (Applicant: University of Central Florida Research Foundation // Inventors—James Hickman, et al)(5 pages).
Communication pursuant to Rules 161(2) and 162 EPC issued on Dec. 18, 2012 for European Patent Application No. 11772857.6, which caims priority to PCT/US11/35585, which published as WO 2011/133985 on Oct. 27, 2011 (Applicant: University of Central Florida Research Foundation // Inventors—James Hickman, et al)(2 pages).
Response to Communication pursuant to Rules 161(2) and 162 EPC filed Aug. 2, 2012 for European Patent Application No. 11772857.6, which caims priority to PCT/US11/35585, which published as WO 2011/133985 on Oct. 27, 2011 (Applicant: University of Central Florida Research Foundation // Inventors—James Hickman, et al).
Restriction Requirement issued Jul. 19, 2012 for U.S. Appl. 12/765,399, filed Apr. 22, 2010 (Hickman, et al—inventors)(7 pages).
Response to Restriction Requirement filed Aug. 17, 2012 for U.S. Appl. No. 12/765,399, filed Apr. 22, 2010 (Hickman, et al—inventors)(5 pages).
Non-Final Office Action issued Oct. 18, 2012 for U.S. Appl. 12/765,399, filed Apr. 22, 2010 (Hickman, et al—inventors)(9 pages).
Response to Non-Final Office Action filed Jan. 16, 2013 for U.S. Appl. No. 12/765,399, filed Apr. 22, 2010 (Hickman, et al—inventors)(49 pages).
Final Office Action issued Apr. 15, 2013 for U.S. Appl. No. 12/765,399, filed Apr. 22, 2010 (Hickman, et al—inventors)(7 pages).

(56) References Cited

OTHER PUBLICATIONS

Response to Final Office Action filed Aug. 15, 2013 for U.S. Appl. No. 12/765,399, filed Apr. 22, 2010 (Hickman, et al—inventors)(6 pages).
International Search Report issued Jul. 30, 2010 for PCT Application No. PCT/US2010/36336, which published as WO 2010/138679 on Dec. 2, 2010 (Applicant: University of Central Florida Research Foundation // Inventors—James Hickman, et al)(2 Pages).
Written Opinion issued Jul. 30, 2010 for PCT Application No. PCT/US2010/036336, which published as WO 2010/138679 on Dec. 2, 2010 (Applicant: University of Central Florida Research Foundation // Inventors—James Hickman, et al)(4 Pages).
International Preliminary Report on Patentability issued Nov. 29, 2011 for PCT Application No. PCT/US2010/036336, which published as WO 2010/138679 on Dec. 2, 2010 (Applicant: University of Central Florida Research Foundation // Inventors—James Hickman, et al)(5 Pages).
Preliminary Amendment filed Nov. 28, 2011 for U.S. Appl. No. 13/322,911, filed Nov. 28, 2011 (Hickman, et al—inventors)(4 pages).
Non-Final Office Action issued Sep. 10, 2013 for U.S. Appl. No. 13/322,911, filed Nov. 28, 2011 (Hickman, et al—inventors)(14 pages).
Communication conveying Extended European Search Report issued Jan. 22, 2013 for EP Application No. 10781190.3, which claims priority to PCT/US2010/036336 filed on May 27, 2010 (Applicant —University of Central Florida Research Foundation// Inventors—James Hickman et al.) (6 Pages).
Restriction Requirement issued Jul. 19, 2012 for U.S. Appl. No. 12/765,399, filed Apr. 22, 2010 (Hickman, et al—inventors)(7 pages).
Non-Final Office Action issued Oct. 18, 2012 for U.S. Appl. No. 12/765,399, filed Apr. 22, 2010 (Hickman, et al—inventors)(9 pages).
Restriction Requirement issued Sep. 14, 2012 for U.S. Appl. No. 12/788,732, filed May 27, 2010 (Hickman, et al—inventors)(5 pages).
Response to Restriction Requirement filed Nov. 14, 2012 for U.S. Appl. No. 12/788,732, filed May 27, 2010 (Hickman, et al—inventors)(6 pages).
Non-Final Office Action issued Feb. 28, 2013 for U.S. Appl. No. 12/788,732, filed May 27, 2010 (Hickman, et al—inventors)(6 pages).
Response to Non-Final Office Action filed May 28, 2013 for U.S. Appl. No. 12/788,732, filed May 27, 2010 (Hickman, et al—inventors)(11 pages).
Final Office Action issued Sep. 16, 2013 for U.S. Appl. No. 12/788,732, filed May 27, 2010 (Hickman, et al—inventors)(5 pages).
International Search Report issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(2 Pages).
Written Opinion issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(5 Pages).
International Preliminary Report on Patentability issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(6 Pages).
Preliminary Amendment filed Nov. 28, 2011 for U.S. Appl. No. 13/322,903, filed Nov. 28, 2011 (Hickman and Davis—inventors)(4 pages).
Restriction Requirement issued Nov. 27, 2012 for U.S. Appl. No. 13/322,903, filed Nov. 28, 2011 (Hickman and Davis—inventors)(6 pages).
Response to Restriction Requirement filed Dec. 1, 2012 for U.S. Appl. No. 13/322,903, filed Nov. 28, 2011 (Hickman and Davis—inventors)(6 pages).
Non-Final Office Action issued Jan. 31, 2013 for U.S. Appl. No. 13/322,903, filed Nov. 28, 2011 (Hickman and Davis—inventors)(17 pages).
Response to Non-Final Office Action filed Jul. 31, 2013 for U.S. Appl. No. 13/322,903, filed Nov. 28, 2011 (Hickman and Davis—inventors)(15 pages).
Communication pursuant to Rules 161(2) and 162 EPC issued on Jan. 23, 2012 for European Patent Application No. 10781254.7, which caims priority to PCT/US2010/36505 filed on May 28, 2010 (Applicant—University of Central Florida Research Foundation// Inventors—James Hickman and Hedvika Davis )(2 pages).
Response to Communication pursuant to Rules 161(2) and 162 EPC filed Aug. 2, 2012 for European Patent Application No. 10781254.7, which caims priority to PCT/US2010/36505 filed on May 28, 2010 (Applicant—University of Central Florida Research Foundation// Inventors—James Hickman and Hedvika Davis )(5 pages).
International Search Report issued Jun. 7, 2011 for PCT Application No. PCT/US2011/023921, which published as WO 2011/097574 on Aug. 11, 2011 (Applicant: University of Central Florida Research Foundation // Inventors—James Hickman, et al)(3 Pages).
Written Opinion issued Jun. 7, 2011 for PCT Application No. PCT/US2011/023921, which published as WO 2011/097574 on Aug. 11, 2011 (Applicant: University of Central Florida Research Foundation // Inventors—James Hickman, et al)(5 Pages).
International Preliminary Report on Patentability issued Aug. 7, 2012 for PCT Application No. PCT/US2011/023921, which published as WO 2011/097574 on Aug. 11, 2011 (Applicant: University of Central Florida Research Foundation // Inventors—James Hickman, et al)(6 Pages).
Preliminary Amendment filed Aug. 1, 2012 for U.S. Appl. No. 13/576,442, filed Aug. 1, 2012 (Hickman, et al—inventors)(4 pages).
Communication pursuant to Rules 161(2) and 162 EPC issued on Oct. 10, 2012 for European Patent Application No. 11740493.9, which caims priority to PCT/US2011/023921 filed on Feb. 7, 2011 (Applicant—University of Central Florida Research Foundation// Inventors—James Hickman, et al)(2 pages).
Response to Communication pursuant to Rules 161(2) and 162 EPC issued on Oct. 10, 2012 for European Patent Application No. 11740493.9, which caims priority to PCT/US2011/023921 filed on Feb. 7, 2011 (Applicant—University of Central Florida Research Foundation// Inventors—James Hickman, et al)(4 pages).
Communication conveying Extended European Search Report issued Jul. 10, 2013 for EP Application No. 11740493.9, which claims priority to PCT/US2011/023921 filed on Feb. 7, 2011 (Applicant—University of Central Florida Research Foundation// Inventors—James Hickman, et al)(7 Pages).
International Search Report issued Oct. 16, 2012 for PCT Application No. PCT/US2012/038358, which published as WO 2012/158923 on Nov. 22, 2012 (Applicant: University of Central Florida Research Foundation // Inventors—James Hickman, et al)(4 Pages).
Written Opinion issued Oct. 16, 2012 for PCT Application No. PCT/US2012/38358, which published as WO 2012/158923 on Nov. 22, 2012 (Applicant: University of Central Florida Research Foundation // Inventors—James Hickman, et al)(6 Pages).
Abbanat D, et al. (2003) Novel antibacterial agents for the treatment of serious Gram-positive infections. Expert Opin Investig Drugs. 12: 379-399.
Abdi H. (2003) Multivariate Analysis. Encyclopedia of Social Sciences Research Methods. M. Lewis-Beck, A. Bryman and T. Futing. Thousand Oaks (CA), Sage.
Adell A, et al. (2002) Origin and functional role of the extracellular serotonin in the midbrain raphe nuclei. Brain Res Brain Res Rev. 39: 154-180.
Agarwal A, et al. (2013) Microfluidic heart on a chip for higher throughput pharmacological studies. Lab Chip. 13: 3599-3608.
Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

(56) References Cited

OTHER PUBLICATIONS

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study of long-term drug effects on synaptic activity. Drug Development Research. 68: 84-93.

Ainscow EK, et al. (1999) Internal regulation of ATP turnover, glycolysis and oxidative phosphorylation in rat hepatocytes. Eur J Biochem. 266: 737-749.

Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol. 38.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R, et al. (2003) The topology of the regulatory interactions predicts the expression pattern of the segment polarity genes in *Drosophila melanogaster*. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) An atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

Alterio J, et al. (1990) Acidic and basic fibroblast growth factor mRNAs are expressed by skeletal muscle satellite cells.Biochem Biophys Res Commun. 166: 1205-1212.

Altmann L. (2000) Multielectrode recordings of synaptic plasticity in brain slices: A new method for the assessment of neurotoxic effects. European Journal of Neuroscience. 12: 29-29.

Amarenco P, et al. (2006) High-dose atorvastatin after stroke or transient ischemic attack. N Engl J Med. 355: 549-559.

Amit M. (2007) Feeder-layer free culture system for human embryonic stem cells. Methods Mol Biol. 407: 11-20.

Anderson DJ, et al. (1997) Cell lineage determination and the control of neuronal identity in the neural crest. Cold Spring Harb Symp Quant Biol. 62: 493-504.

Anderson JE, et al. (1991) Distinctive patterns of basic fibroblast growth factor (bFGF) distribution in degenerating and regenerating areas of dystrophic (mdx) striated muscles. Dev Biol. 147: 96-109.

Andersson H and van den Berg A. (2004) Microfabrication and microfluidics for tissue engineering: state of the art and future opportunities. Lab Chip. 4: 98-103.

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Aracil A, et al. (2004) Proceedings of Neuropeptides 2004, the XIV European Neuropeptides Club meeting. Neuropeptides. 38: 369-371.

Archer JD, et al. (2006) Persistent and improved functional gain in mdx dystrophic mice after treatment with L-arginine and deflazacort. FASEB J. 20: 738-740.

Armstrong DL, et al. (1999) Ion channel regulation. Introduction. Adv Second Messenger Phosphoprotein Res. 33: ix-xx.

Arnold HH, et al. (1998) Muscle differentiation: more complexity to the network of myogenic regulators. Curr Opin Genet Dev. 8: 539-544.

Arnone MI, et al. (1997) The hardwiring of development: organization and function of genomic regulatory systems. Development. 124: 1851-1864.

Arsic N, et al. (2004) Vascular endothelial growth factor stimulates skeletal muscle regeneration in vivo. Mol Ther. 10: 844-854.

Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.

Asotra K, et al. (1993) Protein kinase C activity modulates myelin gene expression in enriched oligodendrocytes. J Neurosci Res. 34: 571-588.

Azzouz M, et al. (2004) VEGF delivery with retrogradely transported lentivector prolongs survival in a mouse ALS model. Nature. 429: 413-417.

Badie N, et al. (2009) A method to replicate the microstructure of heart tissue in vitro using DTMRI-based cell micropatterning. Ann Biomed Eng. 37: 2510-2521.

Bahr M, et al. (1991) In vitro myelination of regenerating adult rat retinal ganglion cell axons by Schwann cells. Glia. 4: 529-533.

Baker DC, et al. (2002) The origin and neuronal function of in vivo nonsynaptic glutamate. J Neurosci. 22: 9134-9141.

Bandi E, et al. (2008) Neural agrin controls maturation of the excitation-contraction coupling mechanism in human myotubes developing in vitro. Am J Physiol Cell Physiol. 294: C66-C73.

Bansal R, et al. (1992) Novel stage in the oligodendrocyte lineage defined by reactivity of progenitors with R-mAb prior to O1 anti-galactocerebroside. J Neurosci Res. 32: 309-316.

Baraban SC, et al. (1997) Osmolarity modulates K+ channel function on rat hippocampal interneurons but not CA1 pyramidal neurons. J Physiol. 498: 679-689.

Barbulovic-Nad I, et al. (2008) Digital microfluidics for cell-based assays. Lab Chip. 8: 519-526.

Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.

Barone FC, et al. (1998) Ischemic preconditioning and brain tolerance: temporal histological and functional outcomes, protein synthesis requirement, and interleukin-1 receptor antagonist and early gene expression. Stroke. 29: 1937-1950; discussion 1950-1951.

Behar TN. (2001) Analysis of fractal dimension of O2A glial cells differentiating in vitro. Methods. 24: 331-339.

Belardinelli L, et al. (2003) Assessing predictors of drug-induced torsade de pointes. Trends Pharmacol Sci. 24: 619-625.

Bellamkonda R, et al. (1995) Hydrogel-based three-dimensional matrix for neural cells. J Biomed Mater Res. 29: 663-671.

Bellas E, et al. (2012) In vitro 3D full-thickness skin-equivalent tissue model using silk and collagen biomaterials. Macromol Biosci. 12: 1627-1236.

Benabid AI. (2003) Deep brain stimulation for Parkinson's disease. Curr Opin Neurobiol. 13: 696-706.

Bender A, et al. (2007) Analysis of pharmacology data and the prediction of adverse drug reactions and off-target effects from chemical structure. ChemMedChem. 2: 861-873.

Bentley A, et al A. (2001) Whole cell biosensors—electrochemical and optical approaches to ecotoxicity testing. Toxicol In Vitro. 15: 469-475.

Berg MC, et al. (2004) Controlling mammalian cell interactions on patterned polyelectrolyte multilayer surfaces. Langmuir. 20: 1362-1368.

Berger TW, et al. (2001) Brain-implantable biomimetic electronics as the next era in neural prosthetics. Proceedings of the IEEE. 89: 993-1012.

Bernstein M, et al. (1996) Receptor-mediated calcium signalling in glial cells from mouse corpus callosum slices. J Neurosci Res. 46: 152-163.

Bers DM. (2002) Cardiac excitation-contraction coupling. Nature. 415: 198-205.

(56) References Cited

OTHER PUBLICATIONS

Bettinger CJ, et al. (2009) Engineering substrate topography at the micro- and nanoscale to control cell function. Angew Chem Int Ed Engl. 48: 5406-5415.
Bhalla US, et al. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN, et al. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by muscle-derived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (O-2A) progenitor cells. Proc Natl Acad Sci U S A. 87: 6368-6372.
Boillee S, et al. (2006) ALS: a disease of motor neurons and their nonneuronal neighbors. Neuron. 52: 39-59.
Boldin SA, et al. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle development and neuromuscular diseases Kloster Irsee, Germany, Sep. 26-Oct. 1, 1999. EMBO J. 19: 1935-1941.
Brand-Saberi B, et al. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.

Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neurol. 159: 237-247.
Brito-Martins M, et al. (2008) beta(1)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters-1 and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA and Vunjak-Novakovic G. (2008) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatology. 45: 1229-1239.
Caiozzo VJ, at el. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ, et al. (2001) Therapeutic drug monitoring: antiarrhythmic drugs. Br J Clin Pharmacol. 52 Suppl 1: 21S-34S.
Camu W, et al. (1992) Purification of embryonic rat motoneurons by panning on a monoclonal antibody to the low-affinity NGF receptor. J Neurosci Methods. 44: 59-70.
Camu W, et al. (1994) Rapid purification of embryonic rat motoneurons: an in vitro model for studying MND/ALS pathogenesis. J Neurol Sci. 124 Suppl: 73-74.
Cannon JG. (1998) Intrinsic and extrinsic factors in muscle aging. Ann N Y Acad Sci. 854: 72-77.
Caratsch CG, et al. (1994) Interferon-alpha, beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.

(56) References Cited

OTHER PUBLICATIONS

Carrasco DI and English AW. Neurotrophin 4/5 is required for the normal development of the slow muscle fiber phenotype in the rat soleus. J Exp Biol. 206: 2191-2200.

Caspi O, et al. (2009) In vitro electrophysiological drug testing using human embryonic stem cell derived cardiomyocytes. Stem Cells Dev. 18: 161-172.

Catoire H, et al. (2008) Sirtuin inhibition protects from the polyalanine muscular dystrophy protein PABPN1. Hum Mol Genet. 17: 2108-2117.

Cerignoli F, et al. (2012) High throughput measurement of $Ca^{2+}$ dynamics for drug risk assessment in human stem cell-derived cardiomyocytes by kinetic image cytometry. J Pharmacol Toxicol Methods. 66: 246-256.

Chambers SM, et al. (2009) Highly efficient neural conversion of human ES and iPS cells by dual inhibition of SMAD signaling. Nat Biotechnol. 27: 275-280.

Chandran S, et al. (1998) Regional potential for oligodendrocyte generation in the rodent embryonic spinal cord following exposure to EGF and FGF-2. Glia. 24: 382-389.

Chang JC, et al. (2001) Modulation of neural network activity by patterning. Biosens Bioelectron. 16: 527-533.

Charpentier A, et al. (1993) RRR-alpha-tocopheryl succinate inhibits proliferation and enhances secretion of transforming growth factor-beta (TGF-beta) by human breast cancer cells. Nutr Cancer. 19: 225-239.

Chaudhary KW, et al. (2006) Embryonic stem cells in predictive cardiotoxicity: laser capture microscopy enables assay development. Toxicol Sci. 90: 149-158.

Chaves M, et al. (2005) Robustness and fragility of Boolean models for genetic regulatory networks. J Theor Biol. 235: 431-449.

Chaves M, et al. (2006) Methods of robustness analysis for Boolean models of gene control networks. Syst Biol (Stevenage). 153: 154-167.

Chen CS, et al. (1997) Geometric control of cell life and death. Science. 276: 1425-1428.

Chen EW, et al. (1995) Target regulation of a motor neuron-specific epitope. J Neurosci. 15: 1555-1566.

Chen J and von Bartheld CS. (2004) Role of exogenous and endogenous trophic factors in the regulation of extraocular muscle strength during development.Invest Ophthalmol Vis Sci. 45: 3538-3545.

Chen QS, et al. (2000) Impairment of hippocampal long-term potentiation by Alzheimer amyloid beta-peptides. J Neurosci Res. 60: 65-72.

Chen X, et al. (2005) Dedifferentiation of adult human myoblasts induced by ciliary neurotrophic factor in vitro. Moll Biol Cell. 16: 3140-3151.

Chen XF, et al. (2008) Dynamic simulation of the effect of calcium-release activated calcium channel on cytoplasmic Ca2+ oscillation. Biophys Chem. 136: 87-95.

Chen XP, (2003) [Exogenous rhCNTF inhibits myoblast differentiation of skeletal muscle of adult human in vitro]. Sheng Li Xue Bao. 55: 464-468.

Chiu AY, et al. (1993) A motor neuron-specific epitope and the low-affinity nerve growth factor receptor display reciprocal patterns of expression during development, axotomy, and regeneration. J Comp Neurol. 328: 351-363.

Choi-Lundberg DL and Bohn MC. (1995) Ontogeny and distribution of glial cell line-derived neurotrophic factor (GDNF) mRNA in rat. Brain Res Dev Brain Res. 85: 80-88.

Choudhury A, et al. (2007) a piezoresistive microcantilever array for surface stress measurement: curvature model and fabrication. J Micromech Microeng. 17: 2065-2076.

Chow I and Poo MM. (1985) Release of acetylcholine from embryonic neurons upon contact with muscle cell. J Neurosci. 5: 1076-1082.

Christ B and Brand-Seberi B. (2002) Limb muscle development. Int J Dev Biol. 46: 905-914.

Cizkova D, et al. (2007) Functional recovery in rats with ischemic paraplegia after spinal grafting of human spinal stem cells. Neuroscience. 147: 546-560.

Clegg CH, et al. (1987) Growth factor control of skeletal muscle differentiation: commitment to terminal differentiation occurs in G1 phase and is repressed by fibroblast growth factor. J Cell Biol. 105: 949-956.

Clements JD, et al. (1992) The time course of glutamate in the synaptic cleft. Science. 258: 1498-1501.

Coggan JS, et al. (2005) Evidence for ectopic neurotransmission at a neuronal synapse. Science. 309: 446-451.

Cohen RI and Almazan G. (1993) Norepinephrine-stimulated PI hydrolysis in oligodendrocytes is mediated by alpha 1A-adrenoceptors. Neuroreport. 4: 1115-1118.

Cohen-Cory S. (2002) The developing synapse: construction and modulation of synaptic structures and circuits. Science. 298: 770-776.

Collins CA and Morgan JE. (2003) Duchenne's muscular dystrophy: animal models used to investigate pathogenesis and develop therapeutic strategies. Int J Exp Pathol. 84: 165-172.

Colomar A and Robitaille R. (2004) Glial modulation of synaptic transmission at the neuromuscular junction. Glia. 47: 284-289.

Cooper A, et al. (1976) The growth of mouse neuroblastoma cells in controlled orientations on thin films of silicon monoxide. Exp Cell Res. 103: 435-439.

Corey JM, et al. (1991) Compliance of hippocampal neurons to patterned substrate networks. J Neurosci Res. 30: 300-307.

Corey JM, et al. (1996) Micrometer resolution silane-based patterning of hippocampal neurons: critical variables in photoresist and laser ablation processes for substrate fabrication. IEEE Trans Biomed Eng. 43: 944-955.

Corey JM, et al. (1997) Differentiated B104 neuroblastoma cells are a high-resolution assay for micropatterned substrates. J Neurosci Methods. 75: 91-97.

Cortassa S, et al. (2003) An integrated model of cardiac mitochondrial energy metabolism and calcium dynamics. Biophys J. 84: 2734-2755.

Cossu G, et al. (1996) How is myogenesis initiated in the embryo? Trends Genet. 12: 218-223.

Courdier-Fruh I, et al. (2002) Glucocorticoid-mediated regulation of utrophin levels in human muscle fibers. Neuromuscul Disord. 12(Suppl 1): S95-S104.

Cross-Doersen D and Isfort RJ. (2003) A novel cell-based system for evaluating skeletal muscle cell hypertrophy-inducing agents. In Vitro Cell Dev Biol Animal. 39: 407-412.

Cukierman E, et al. (2002) Cell interactions with three-dimensional matrices. Curr Opin Cell Biol. 14: 633-639.

Cunningham JJ and Roussel MF. (2001) Cyclin-dependent kinase inhibitors in the development of the central nervous system. Cell Growth Differ. 12: 387-396.

Cuppini R, et al. (2001) Alpha-tocopherol controls cell proliferation in the adult rat dentate gyms. Neurosci Lett. 303: 198-200.

Currie PD and Ingham PW. (1996) Induction of a specific muscle cell type by a hedgehog-like protein in zebrafish. Nature. 382: 452-455.

Curtis R, et al. (1988) Development of macroglial cells in rat cerebellum. I. Use of antibodies to follow early in vivo development and migration of oligodendrocytes. J Neurocytol. 17: 43-54.

Cysyk J and Tung L. (2008) Electric field perturbations of spiral waves attached to millimeter-size obstacles. Biophys J. 94: 1533-1541.

Dakhel Y and Jamali F. (2006) Erythromycin potentiates PR interval prolonging effect of verapamil in the rat: a pharmacodynamic drug interaction. Toxicol Appl Pharmacol. 214: 24-29.

Daniels MP, et al. (2000) Rodent nerve-muscle cell culture system for studies of neuromuscular junction development: refinements and applications. Microsc Res Tech. 49: 26-37.

Daniels MP. (1990) Localization of actin, beta-spectrin, 43 × 10(3) Mr and 58 × 10(3) Mr proteins to receptor-enriched domains of newly formed acetylcholine receptor aggregates in isolated myotube membranes. J Cell Sci. 97(Pt 4): 615-626.

Daniels MP. (1997) Intercellular communication that mediates formation of the neuromuscular junction. Mol Neurobiol. 14: 143-170.

(56) References Cited

OTHER PUBLICATIONS

Das M, et al. (2003) Electrophysiological and morphological characterization of rat embryonic motoneurons in a defined system. Biotechnol Prog. 19: 1756-1761.
Das M, et al. (2004) Long-term culture of embryonic rat cardiomyocytes on an organosilane surface in a serum-free medium. Biomaterials. 25: 5643-5647.
Das M, et al. (2005) Adult rat spinal cord culture on an organosilane surface in a novel serum-free medium. In Vitro Cell Dev Biol Anim. 41: 343-348.
Das M, et al. (2006) A defined system to allow skeletal muscle differentiation and subsequent integration with silicon microstructures. Biomaterials. 27: 4374-4380.
Das M, et al. (2007a) Auto-catalytic ceria nanoparticles offer neuroprotection to adult rat spinal cord neurons. Biomaterials. 28: 1918-1925.
Das M, et al. (2007b) Differentiation of skeletal muscle and integration of myotubes with silicon microstructures using serum-free medium and a synthetic silane substrate. Nat Protoc. 2: 1795-1801.
Das M, et al. (2007c) Embryonic motoneuron-skeletal muscle co-culture in a defined system. Neuroscience. 146: 481-488.
Das M, et al. (2008) Temporal neurotransmitter conditioning restores the functional activity of adult spinal cord neurons in long-term culture. Exp Neurol. 209: 171-180.
Das M, et al. (2009a) Developing a novel serum-free cell culture model of skeletal muscle differentiation by systematically studying the role of different growth factors in myotube formation. In Vitro Cell Dev Biol Anim. 45: 378-387.
Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.
Das M, et al. (2010) A defined long-term in vitro tissue engineered model of neuromuscular junctions. Biomaterials. 31: 4880-4888.
Datar R, et al. (2009) Cantilever Sensors: Nanomechanical Tools for Diagnostics. MRS Bulletin. 34: 449-454.
David JA and Pitman RM. (1982) The effects of axotomy upon the extrasynaptic acetylcholine sensitivity of an identified motoneurone in the cockroach Periplaneta americana. J Exp Biol. 98: 329-341.
Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.
De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.
De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.
de Lange P, et al. (2006) Sequential changes in the signal transduction responses of skeletal muscle following food deprivation. FASEB J. 20: 2579-2581.
de Wilde J, et al. (2008) Short-term high fat-feeding results in morphological and metabolic adaptations in the skeletal muscle of C57BL/6J mice. Physiol Genomics. 32: 360-369.
Dell'Era P, et al. (2003) Fibroblast growth factor receptor-1 is essential for in vitro cardiomyocyte development. Circ Res. 93: 414-420.
Denning C and Anderson D. (2008) Cardiomyocytes from human embryonic stem cells as predictors of cardiotoxicity. Drug Discovery Today: Therapeutic Strategies. 5: 223-232.
Dennis Rg and Kosnik IPE. (2000) Excitability and isometric contractile properties of mammalian skeletal muscle constructs engineered in vitro. In Vitro Cell Dev Biol Anim. 36: 327-335.
Dennis RG, et al. (2001) Excitability and contractility of skeletal muscle engineered from primary cultures and cell lines. Am J Physiol Cell Physiol. 280: C288-C295.

Denyer MCT, et al. (1998) Preliminary study on the suitability of a pharmacological bio-assay based on cardiac myocytes cultured over microfabricated microelectrode arrays. Med Biol Eng Comput. 36: 638-644.
Descarries L, et al. (1997) Diffuse transmission by acetylcholine in the CNS. Prog Neurobiol. 53: 603-625.
Dhavan R and Tsai L. (2001) A decade of CDK5. Nat Rev Mol Cell Biol. 2: 749-759.
Dhir V, et al. (2009) Patterning of diverse mammalian cell types in serum free medium with photoablation. Biotechnol Prog. 25: 594-603.
Di Giovanni S, et al. (2005) Cell cycle inhibition provides neuroprotection and reduces glial proliferation and scar formation after traumatic brain injury. Proc Natl Acad Sci U S A. 102: 8333-8338.
Dimitrova DS and Gilbert DM. (2000) Temporally coordinated assembly and disassembly of replication factories in the absence of DNA synthesis. Nat Cell Biol. 2: 686-694.
Djouhri L and Lawson SN. (1999) Changes in somatic action potential shape in guinea-pig nociceptive primary afferent neurones during inflammation in vivo. J Physiol. 520 Pt 2: 565-576.
Dolcet X, et al. (2001) Cytokines promote motoneuron survival through the Janus kinase-dependent activation of the phosphatidylinositol 3-kinase pathway. Mol Cell Neurosci. 18: 619-631.
Du Y, et al. (2006) Distinct effects of p75 in mediating actions of neurotrophins on basal forebrain oligodendrocytes. Mol Cell Neurosci. 31: 366-375.
Dulcey CS, et al. (1991) Deep UV photochemistry of chemisorbed monolayers: patterned coplanar molecular assemblies. Science. 252: 551-554.
Dumont RJ, et al. (2001) Acute spinal cord injury, part I: pathophysiologic mechanisms. Clin Neuropharmacology. 24: 254-264.
Duport S, et al. (1999) A metallic multisite recording system designed for continuous long-term monitoring of electrophysiological activity in slice cultures. Biosens Bioelectron. 14: 369-376.
Dusterhoft S and Pette D. (1999) Evidence that acidic fibroblast growth factor promotes maturation of rat satellite-cell-derived myotubes in vitro. Differentiation. 65 : 161-169.
Dutton EK, et al. (1995) Acetylcholine receptor aggregation at nerve-muscle contacts in mammalian cultures: induction by ventral spinal cord neurons is specific to axons. J Neurosci. 15: 7401-7416.
Edwards D, et al. (2010) Addition of glutamate to serum-free culture promotes recovery of electrical activity in adult hippocampal neurons in vitro. J Neurosci Methods. 190: 155-163.
Egert U, et al. (1998) A novel organotypic long-term culture of the rat hippocampus on substrate-integrated multielectrode arrays. Brain Res Brain Res Protoc. 2: 229-242.
Egert U, et al. (2006) Analysis of cardiac myocyte activity dynamics with microeletrode arrays. In: Taketani M BM, editor. Advances in netwrok electrophysiology using multi electrode arrays: Springer 2006. p. 274-290.
Eisen A and Swash M. (2001) Clinical neurophysiology of ALS. Clin Neurophysiol. 112: 2190-2201.
Eisenberg T, et al. (2009) Induction of autophagy by spermidine promotes longevity. Nat Cell Biol. 11: 1305-1314.
Eldridge CF, et al. (1989) Differentiation of axon-related Schwann cells in vitro: II. Control of myelin formation by basal lamina. J Neurosci. 9: 625-638.
Elia D, et al. (2007) Sonic hedgehog promotes proliferation and differentiation of adult muscle cells: Involvement of MPAK/ERK and PI3K/Akt pathways. Biochim Biophys Acta. 1773: 1438-1446.
Emery AEH. (2002) the muscular dystrophies. Lancet. 359: 687-695.
Engler AJ, et al. (2006) Matrix elasticity directs stem cell lineage specification. Cell. 126: 677-689.
English AW. (2003) Cytokines, growth factors and sprouting at the neuromuscular junction. J Neurocytol. 32: 943-960.
Entcheva EK, et al. (2004) Fluorescence imaging of electrical activity in cardiac cells using an all-solid-state system. IEEE Trans Biomed Eng. 51: 331-341.
Ericson J, et al. (1992) Early stages of motor neuron differentiation revealed by expression of homeobox gene Islet-1. Science. 256: 1555-1560.

(56) References Cited

OTHER PUBLICATIONS

Esch MB, et al. (2011) The role of body-on-a-chip devices in drug and toxicity studies. Annu Rev Biomed Eng. 13: 55-72.
Esch MB, et al. (2012) On chip porous polymer membranes for integration of gastrointestinal tract epithelium with microfluidic 'body-on-a-chip' devices. Biomed Microdevices. 14: 895-906.
Eschenhagen T and Zimmermann WH. (2005) Engineering myocardial tissue. Circ Res. 97: 1220-1231.
Evans MS, et al. (1998) Electrophysiology of embryonic, adult and aged rat hippocampal neurons in serum-free culture. J Neurosci Methods. 79: 37-46.
Fan CM and Tessier-Lavigne M. (1994) Patterning of mammalian somites by surface ectoderm and notochord: evidence for sclerotome induction by a hedgehog homolog. Cell. 79: 1175-1186.
Faraut B, et al. (2004) Thrombin reduces MuSK and acetylcholine receptor expression along with neuromuscular contact size in vitro. Eur J Neurosci. 19: 2099-2108.
FDA (2004) Innovation or Stagnation: Challenge and Opportunity on the Critical Path to New Medical Products.
Fernandez-Valle C, et al. (1993) Expression of the protein zero myelin gene in axon-related Schwann cells is linked to basal lamina formation. Development. 119: 867-880.
Fernandez-Valle C, et al. (1995) Schwann cells degrade myelin and proliferate in the absence of macrophages: evidence from in vitro studies of Wallerian degeneration. J Neurocytol. 24: 667-679.
Fields GB, et al. (1998) Protein-like molecular architecture: biomaterial applications for inducing cellular receptor binding and signal transduction. Biopolymers. 47: 143-151.
Fields GB. (1999) Induction of protein-like molecular architecture by self-assembly processes. Bioorg Med Chem. 7: 75-81.
Figenschou A, et al. (1996) Cholinergic modulation of the action potential in rat hippocampal neurons. Eur J Neurosci. 8: 211-219.
Fink CC, et al. (1999) Determination of time-dependent inositol-1,4,5-trisphosphate concentrations during calcium release in a smooth muscle cell. Biophys J. 77: 617-628.
Fischbach GD and Cohen SA. (1973) The distribution of acetylcholine sensitivity over uninnervated and innervated muscle fibers grown in cell culture. Dev Biol. 31: 147-162.
Fischbach GD. (1972) Synapse formation between dissociated nerve and muscle cells in low density cell cultures. Dev Biol. 28: 407-429.
Fisher OZ, et al. (2010) Bioinspired materials for controlling stem cell fate. Acc Chem Res. 43: 419-428.
Fishman RA. (2002) The cerebrospinal fluid production rate is reduced in dementia of the Alzheimer's type. Neurology. 58: 1866; author reply 1866.
Flucher BE, et al. (1990) Localization of the alpha 1 and alpha 2 subunits of the dihydropyridine receptor and ankyrin in skeletal muscle triads. Neuron. 5: 339-351.
Flucher BE, et al. (1991) Biogenesis of transverse tubules in skeletal muscle in vitro. Dev Biol. 145: 77-90.
Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.
Flucher BE, et al. (1994) Molecular organization of transverse tubule/sarcoplasmic reticulum junctions during development of excitation-contraction coupling in skeletal muscle. Mol Biol Cell. 5: 1105-1118.
Forry SP, et al. (2006) Facilitating the culture of mammalian nerve cells with polyelectrolyte multilayers. Langmuir. 22: 5770-5775.
Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.
Fowler VM, et al. (1993) Tropomodulin is associated with the free (pointed) ends of the thin filaments in rat skeletal muscle. J Cell Biol. 120: 411-420.
Fox MA, et al. (2007) Distinct target-derived signals organize formation, maturation, and maintenance of motor nerve terminals. Cell. 129: 179-193.
Francis PT. (2008) Glutamatergic approaches to the treatment of cognitive and behavioural symptoms of Alzheimer's disease. Neurodegener Dis. 5: 241-243.
Frank E and Fischbach Gd. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C and Protasi F. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted Tgf-β ligand. Curr Biol. 22: 1831-1838.
Funakoshi H, et al. (1995) Muscle-derived neurotrophin-4 as an activity-dependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175: 50-57.
Galizia CG and Menzel R. (2000) Probing the olfactory code. Nat Neurosci. 3: 853-854.
Gao BX and Ziskind-Conhaim L. (1995) Development of glycine- and GABA-gated currents in rat spinal motoneurons. J Neurophysiol. 74: 113-121.
Gao BX and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69: 4027-4037.
Gaud A, et al. (2004) Prednisone reduces muscle degeneration in dystrophin-deficient Caenorhabditis elegans. Neuromuscul Disord. 14: 365-370.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kip1) and p21(CIP1) accumulation and G1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass L and Kauffman SA. (1973) the logical analysis of continuous, non-linear biochemical control networks. J Theor Biol. 39: 103-129.
Glass L. (1975) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.

(56) References Cited

OTHER PUBLICATIONS

Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83: 2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374: 1745-1753.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP + PS1 transgenic mice. Neurobiol Dis. 15: 188-195.
Haas HL and Selbach O. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1Lactide and Poly(ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U S A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey JV, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients with atorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.

(56) References Cited

OTHER PUBLICATIONS

Hickman J, et al. (1993) The use of monlayers as templates for biocompatibility studies. Abstracts of Papers of the American Chemical Society. 205: 146-Coll.

Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.

Hickman JJ, et al. (1994) Rational Pattern Design for in-Vitro Cellular Networks Using Surface Photochemistry. J Vac Science Technol A. 12: 607-616.

Hirano A. (1968) A confirmation of the oligodendroglial origin of myelin in the adult rat. J Cell Biol. 38: 637-640.

Hjerling-Leffler J, et al. (2005) The boundary cap: a source of neural crest stem cells that generate multiple sensory neuron subtypes. Development. 132: 2623-2632.

Hoffman EP and Escolar D. (2006) Translating mighty mice into neuromuscular therapeutics: is bigger muscle better? Am J Pathol. 168: 1775-1778.

Hofmann F and Bading H. (2006) Long term recordings with microelectrode arrays: studies of transcription-dependent neuronal plasticity and axonal regeneration. J Physiol Paris. 99: 125-132.

Holleran AL, et al. (1995) Glutamine metabolism in AS-30D hepatoma cells. Evidence for its conversion into lipids via reductive carboxylation. Mol Cell Biochem. 152: 95-101.

Hondeghem LM and Hoffman P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.

Hondeghem LM, et al. (2001) Instability and triangulation of the action potential predict serious proarrhythmia, but action potential duration prolongation is antiarrhythmic. Circulation. 103: 2004-2013.

Hondeghem LM, et al. (2003a) Detection of proarrhythmia in the female rabbit heart: blinded validation. J Cardiovasc Electrophysiol. 14: 287-294.

Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.

Hondeghem LM. (2007) Relative contributions of TRIaD and QT to proarrhythmia. J Cardiovasc Electrophysiol. 18: 655-657.

Hsiao CF, et al. (2005) Voltage-dependent calcium currents in trigeminal motoneurons of early postnatal rats: modulation by 5-HT receptors. J Neurophysiol. 94: 2063-2072.

Hu BY, et al. (2009) Human oligodendrocytes from embryonic stem cells: conserved SHH signaling networks and divergent FGF effects. Development. 136: 1443-1452.

Hua JY and Smth SJ. (2004) Neural activity and the dynamics of central nervous system development. Nat Neurosci. 7: 327-332.

Huang Y, et al. (2007) An alpha1A-adrenergic-extracellular signal-regulated kinase survival signaling pathway in cardiac myocytes. Circulation. 115: 763-772.

Huang YC, et al. (2005) Rapid formation of functional muscle in vitro using fibrin gels. J Appl Physiol. 98: 706-713.

Hucka M, et al. (2003) The systems biology markup language (SBML): a medium for representation and exchange of biochemical network models. Bioinformatics. 19: 524-531.

Hughes B. (2008) 2007 FDA drug approvals: a year of flux. Nat Rev Drug Discov. 7: 107-109.

Huh D, et al. (2010) Reconstituting organ-level lung functions on a chip. Science. 328: 1662-1668.

Huh D, et al. (2012) Microengineered physiological biomimicry: organs-on-chips. Lab Chip. 12: 2156-2164.

Hui EE and Bhatia SN. (2007) Microscale control of cell contact and spacing via three-component surface patterning. Langmuir. 23: 4103-4107.

Hung SC, et al. (2002) In vitro differentiation of size-sieved stem cells into electrically active neural cells. Stem Cells. 20: 522-529.

Husmann I, et al. (1996) Growth factors in skeletal muscle regeneration. Cytokine Growth Factor Rev. 7: 249-258.

Huxley, A. F. (1975). The origin of force in skeletal muscle. Ciba Found Symp. 31: 271-290.

Ichikawa H, et al. (2004) Effect of Brn-3a deficiency on parvalbumin-immunoreactive primary sensory neurons in the dorsal root ganglion. Brain Res Dev Brain Res. 150: 41-45.

Inoue H, et al. (2004) Rapid electrical stimulation of contraction modulates gap junction protein in neonatal rat cultured cardiomyocytes: involvement of mitogen-activated protein kinases and effects of angiotensin II-receptor antagonist. J Am Coll Cardiol. 44: 914-922.

Iravanian S, et al. (2003) Functional reentry in cultured monolayers of neonatal rat cardiac cells. Am J Physiol Heart Circ Physiol. 285: H449-H456.

Ito Y. (1999) Surface micropatterning to regulate cell functions. Biomaterials. 20: 2333-2342.

Izrael M, et al. (2007) Human oligodendrocytes derived from embryonic stem cells: Effect of noggin on phenotypic differentiation in vitro and on myelination in vivo. Mol Cell Neurosci. 34: 310-323.

Izumiya Y, et al. (2008) Fast/glycolytic muscle fiber growth reduces fat mass and improves metabolic parameters in obese mice. Cell Metabolism. 7: 159-172.

Jackson JH 4th, et al. (2004) Assessment of drug therapy management and the prevalence of heart failure in a managed care population with hypertension. J Manag Care Pharm. 10: 513-520.

Jaworska-Wilczynska M, et al. (2002) Three lipoprotein receptors and cholesterol in inclusion-body myositis muscle. Neurology. 58: 438-445.

Jensen J, et al. (2009) Human embryonic stem cell technologies and drug discovery. J Cell Physiol. 219: 513-519.

Jessen KR and Mirsky R. (2005) The origin and development of glial cells in peripheral nerves. Nat Rev Neurosci. 6: 671-682.

Jevsek M, et al. (2004) Origin of acetylcholinesterase in the neuromuscular junction formed in the in vitro innervated human muscle. Eur J Neurosci. 20: 2865-2871.

Jhamandas JH, et al. (2001) Cellular mechanisms for amyloid beta-protein activation of rat cholinergic basal forebrain neurons. J Neurophysiol. 86: 1312-1320.

Jiang XH, et al. (2009) Isolation and characterization of neural crest stem cells derived from in vitro-differentiated human embryonic stem cells. Stem Cells Dev. 18: 1059-1070.

Jiang Z and Clemens PR. (2006) Cellular caspase-8-like inhibitory protein (cFLIP) prevents inhibition of muscle cell differentiation induced by cancer cells. FASEB J. 20: 2570-2572.

Jiang ZG, et al. (1990) Excitatory and inhibitory transmission from dorsal root afferents to neonate rat motoneurons in vitro. Brain Res. 535: 110-118.

Jin P, et al. (1991) Recombinant platelet-derived growth factor-BB stimulates growth and inhibits differentiation of rat L6 myoblasts. J Biol Chem. 266: 1245-1249.

Johnson TE, et al. (2005) Statins and PPARalpha agonists induce myotoxicity in differentiated rat skeletal muscle cultures but do not exhibit synergy with cotreatment. Toxicol Appl Pharmacol. 208: 210-221.

Julius D and Basbaum AI. (2001) Molecular mechanisms of nociception. Nature. 413: 203-210.

Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.

Jung DR, et al. (2001) Topographical and physicochemical modification of material surface to enable patterning of living cells. Crit Rev Biotechnol. 21: 111-154.

Jurdana M, et al. (2009) Neural agrin changes the electrical properties of developing human skeletal muscle cells. Cell Mol Neurobiol. 29: 123-131.

Kaeberlein M. (2009) Spermidine surprise for a long life. Nat Cell Biol. 11: 1277-1278.

Kaji H, et al. (2003) Pharmacological characterization of micropatterned cardiac myocytes. Biomaterials. 24: 4239-4244.

(56) References Cited

OTHER PUBLICATIONS

Kamp TJ. (2009) Human pluripotent stem cell-derived cardiomyocytes for safety pharmacology applications. Journal of Pharmacological and Toxicological Methods. 60: 259.

Kane RS, et al. (1999) Patterning proteins and cells using soft lithography. Biomaterials. 20: 2363-2376.

Kang JH, et al. (2009) In vitro 3D model for human vascularized adipose tissue. Tissue Eng Part A. 15: 2227-2236.

Kato AC and Lindsay RM. (1994) Overlapping and additive effects of neurotrophins and CNTF on cultured human spinal cord neurons. Exp Neurol. 130: 196-201.

Katsuki H, et al. (2000) Distinct signaling pathways involved in multiple effects of basic fibroblast growth factor on cultured rat hippocampal neurons. Brain Res. 885: 240-250.

Katz LC and Shatz CJ. (1996) Synaptic activity and the construction of cortical circuits. 274: 1133-1138.

Kauffman S, et al. (2003) Random Boolean network models and the yeast transcriptional network. Proc Natl Acad Sci U S A. 100: 14796-14799.

Kauffman S. (1971) Gene regulation networks: a theory for their global structure and behaviors. Curr Top Dev Biol. 6: 145-182.

Kaufmann P, et al. (2006) Toxicity of statins on rat skeletal muscle mitochondria. Cell Mol Life Sci. 63: 2415-2425.

Keefer EW, et al. (2001) Acute toxicity screening of novel AChE inhibitors using neuronal networks on microelectrode arrays. Neurotoxicology. 22: 3-12.

Keefer EW, et al. (2001) Characterization of acute neurotoxic effects of trimethylolpropane phosphate via neuronal network biosensors. Biosens Bioelectron. 16: 513-525.

Kessaris N, et al. (2008) Specification of CNS glia from neural stem cells in the embryonic neuroepithelium. Philos Trans R Soc Lond B Biol Sci. 363: 71-85.

Khademhosseini A, et al. (2006a) Interplay of biomaterials and micro-scale technologies for advancing biomedical applications. J Biomater Sci Polym Ed. 17: 1221-1240.

Khademhosseini A, et al. (2006b) Microscale technologies for tissue engineering and biology. Proc Natl Acad Sci USA. 103: 2480-2487.

Khorchid A, et al. (1999) Characterization of the signal transduction pathways mediating noradrenaline-stimulated MAPK activation and c-fos expression in oligodendrocyte progenitors. J Neurosci Res. 58: 765-778.

Khorchid A, et al. (2002) Developmental regulation of alpha 1A-adrenoceptor function in rat brain oligodendrocyte cultures. Neuropharmacology. 42: 685-696.

Kidambi S, et al. (2004) Controlling primary hepatocyte adhesion and spreading on protein-free polyelectrolyte multilayer films. J Am Chem Soc. 126: 16286-16287.

Kidambi S, et al. (2007a) Patterned co-culture of primary hepatocytes and fibroblasts using polyelectrolyte multilayer templates. Macromol Biosci. 7: 344-353.

Kidambi S, et al. (2007b) Cell adhesion on polyelectrolyte multilayer coated polydimethylsiloxane surfaces with varying topographies. Tissue Eng. 13: 2105-2117.

Kidd, J. (2006). Life after statin patent expiries. Nat Rev Drug Discov. 5: 813-814.

Kim C, et al. (2010) Non-cardiomyocytes influence the electrophysiological maturation of human embryonic stem cell-derived cardiomyocytes during differentiation. Stem Cells Dev. 19: 783-795.

Kim J, et al. (2002) Dopamine neurons derived from embryonic stem cells function in an animal model of Parkinson's disease. Nature. 418: 50-56.

Kim K, et al. (2011) Calibrated micropost arrays for biomechanical characterization of cardiomyocytes. Micro and Nano Letters. 6: 317-322.

Kim SU, et al. (2002) Production of immortalized human neural crest stem cells. Methods Mol Biol. 198: 55-65.

King T, et al. (2000) Piezoactuators for 'real-world' applications—Can they deliver sufficient displacement? Power Engineering. 14: 105-110.

Kingshott P and Griesser HJ. (1999) Surfaces that resist bioadhesion. Current Opinion in Solid State and Materials Science. 4: 403-412.

Kirazov E, et al. (2008) Amyloid beta peptides exhibit functional neurotoxicity to cortical network cultures. Compt Rend Acad Bulg Sci. 61: 905-910.

Kita-Matsuo H, et al. (2009) Lentiviral vectors and protocols for creation of stable hESC lines for fluorescent tracking and drug resistance selection of cardiomyocytes. PLoS One. 4: e5046.

Kleber AG and Rudy Y. (2004) Basic mechanisms of cardiac impulse propagation and associated arrhythmias. Physiol Rev. 84: 431-488.

Klein C, et al. (2002) Zinc inhibition of cAMP signaling. J Biol Chem. 277: 11859-11865.

Klein WL. (2002) Abeta toxicity in Alzheimer's disease: globular oligomers (ADDLs) as new vaccine and drug targets. Neurochem Int. 41: 345-352.

Kleinfeld D, et al. (1988) Controlled outgrowth of dissociated neurons on patterned substrates. J Neurosci. 8: 4098-4120.

Knobloch M and Mansuy IM. (2008) Dendritic spine loss and synaptic alterations in Alzheimer's disease. Mol Neurobiol. 37: 73-82.

Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.

Kobayashi T, et al. (1987) Human muscle cultured in monolayer and cocultured with fetal rat spinal cord: importance of dorsal root ganglia for achieving successful functional innervation. J Neurosci. 7: 3131-3141.

Koike T, et al. (2008) Axon & dendrite degeneration: its mechanisms and protective experimental paradigms. Neurochem Int. 52: 751-760.

Koirala S, et al. (2003) Roles of glial cells in the formation, function, and maintenance of the neuromuscular junction. J Neurocytol. 32: 987-1002.

Koleva M, et al. (2005) Pleiotropic effects of sonic hedgehog on muscle satellite cells. Cell Mol Life Sci. 62: 1863-1870.

Koliatsos VE, et al. (2008) Human stem cell grafts as therapies for motor neuron disease. Expert Opin Biol Ther. 8: 137-141.

Kontrogianni-Konstantopoulos A, et al. (2009) Muscle giants: molecular scaffolds in sarcomerogenesis. Physiol Rev. 89: 1217-1267.

Kornblum HI, et al. (1999) Multiple trophic actions of heparin-binding epidermal growth factor (HB-EGF) in the central nervous system. Eur J Neurosci. 11: 3236-3246.

Kucera J and Dorovini-Zis K. (1979). Types of human intrafusal muscle fibers. Muscle Nerve. 2: 437-451.

Kucera J and Walro J. (1992) Axotomy induces fusimotor-free muscle spindles in neonatal rats. Neurosci Lett. 136: 216-218.

Kucera J, et al. (1989) Role of nerve and muscle factors in the development of rat muscle spindles. Am J Anat. 186: 144-160.

Kucera J. (1982a) One-bag-fiber muscle spindles in tenuissimus muscles of the cat. Histochemistry and Cell Biology. 76: 315-328.

Kucera, J. (1982b). The topography of long nuclear chain intrafusal fibers in the cat muscle spindle. Histochemistry. 74: 183-197.

Kucera, J. (1983). Multiple-bag-fiber muscle spindles in tenuissimus muscles of the cat. Histochemistry. 79: 457-476.

Kudla AJ, et al. (1995) A requirement for fibroblast growth factor in regulation of skeletal muscle growth and differentiation cannot be replaced by activation of platelet-derived growth factor signaling pathways. Mol Cell Biol. 15: 3238-3246.

Kuhl U, et al. (1982) Synthesis of type IV collagen and laminin in cultures of skeletal muscle cells and their assembly on the surface of myotubes. Dev Biol. 93: 344-354.

Kuhl U, et al. (1986) Role of laminin and fibronectin in selecting myogenic versus fibrogenic cells from skeletal muscle cells in vitro. Dev Biol. 117: 628-635.

Kumar S, et al. (1998) NT-3-mediated TrkC receptor activation promotes proliferation and cell survival of rodent progenitor oligodendrocyte cells in vitro and in vivo. J Neurosci Res. 54: 754-765.

Kurek JB, et al. (1996) Leukemia inhibitory factor and interleukin-6 are produced by diseased and regenerating skeletal muscle. Muscle Nerve. 19: 1291-1301.

(56) References Cited

OTHER PUBLICATIONS

Lacor PN, et al. (2007) Abeta oligomer-induced aberrations in synapse composition, shape, and density provide a molecular basis for loss of connectivity in Alzheimer's disease. J Neurosci. 27: 796-807.
Lacor PN. (2007) Advances on the understanding of the origins of synaptic pathology in AD. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abetal-42 are potent central nervous system neurotoxins. Proc Natl Acad Sci U S A. 95: 6448-6453.
Lambeth MJ and Kushmerick MJ. (2002) A computational model for glycogenolysis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer R and Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-1 (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5. Proc Natl Acad Sci U S A. 98: 12742-12747.

Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4: e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. Curr Neurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations in DRG neurons: relation to neuropathic pain. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci U S A. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, al. et al (2005) Enantioselectivity in environmental safety of current chiral insecticides. Proc Natl Acad Sci U S A. 102: 701-706.
Lochter AJ, et al. (1995) Control of neuronal morphology in vitro: interplay between adhesive substrate forces and molecular instruction. J Neurosci Res. 42: 145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, al. et al (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit 1C.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Int J Dev Neurosci. 10: 59-73.

(56) References Cited

OTHER PUBLICATIONS

Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.

Machida S, et al. (2004) Primary rat muscle progenitor cells have decreased proliferation and myotube formation during passages. Cell Prolif. 37: 267-277.

Maduell F. (2005) Hemodiafiltration. Hemodial Int. 9: 47-55.

Mahler GJ, et al. (2009a) Characterization of a gastrointestinal tract microscale cell culture analog used to predict drug toxicity. Biotechnol Bioeng. 104: 193-205.

Mahler GJ, et al. (2009b) Characterization of Caco-2 and HT29-MTX cocultures in an in vitro digestion/cell culture model used to predict iron bioavailability. J Nutr Biochem. 20: 494-502.

Malerba A, et al. (2009) Selection of multipotent cells and enhanced muscle reconstruction by myogenic macrophage-secreted factors. Exp Cell Res. 315: 915-927.

Malm C, et al. (2004) Leukocytes, cytokines, growth factors and hormones in human skeletal muscle and blood after uphill or downhill running. J Physiol. 556: 983-1000.

Malo N, et al. (2006) Statistical practice in high-throughput screening data analysis. Nat Biotechnol. 24: 167-175.

Marhl M, et al. (2000) Complex calcium oscillations and the role of mitochondria and cytosolic proteins. Biosystems. 57: 75-86.

Marona HRN, et al. (1999) Determination of sparfloxacin and its degradation products by HPLC-PDA. J Antimicrob Chemother. 44: 301-302.

Marques MJ and Neto HS. (1997) Ciliary neurotrophic factor stimulates in vivo myotube formation in mice. Neurosci Lett. 234: 43-46.

Mars T, et al. (2001) Differentiation of glial cells and motor neurons during the formation of neuromuscular junctions in cocultures of rat spinal cord explant and human muscle. J Comp Neurol. 438: 239-251.

Mars T, et al. (2003) Functional innervation of cultured human skeletal muscle proceeds by two modes with regard to agrin effects. Neuroscience. 118: 87-97.

Martin-Caraballo M and Greer JJ. (2000) Development of potassium conductances in perinatal rat phrenic motoneurons. J Neurophysiol. 83: 3497-3508.

Martinou JC, et al. (1992) Cholinergic differentiation factor (CDF/LIF) promotes survival of isolated rat embryonic motoneurons in vitro. Neuron. 8: 737-744.

Masu Y, et al. (1993) Disruption of the CNTF gene results in motor neuron degeneration. Nature. 365: 27-32.

Matsakas A and Patel K. (2009) Skeletal muscle fibre plasticity in response to selected environmental and physiological stimuli. Histol Histopathol. 24: 611-629.

Matsuda T, et al. (1992) Two-dimensional cell manipulation technology. An artificial neural circuit based on surface microphotoprocessing. ASAIO J. 38: M243-M247.

Matthews PB. (1964) Muscle spindles and their motor control. Physiol Rev. 44: 219-288.

Mattson MP, et al. (1992) Beta-Amyloid Peptides Destabilize Calcium Homeostasis and Render Human Cortical-Neurons Vulnerable to Excitotoxicity. J Neurosci. 12: 376-389.

Matzno S, et al. (2003) Evaluation of the synergistic adverse effects of concomitant therapy with statins and fibrates on rhabdomyolysis. J Pharm Pharmacol. 55: 795-802.

Mayes L, et al. (2007) Pbx homeodomain proteins direct Myod activity to promote fast-muscle differentiation. Development. 134: 3371-3382.

Maynard EM. (2001) Visual prostheses. Annu Rev Biomed Eng. 3: 145-168.

McAuliffe GJ, et al. (2008) Development of a gastrointestinal tract microscale cell culture analog to predict drug transport. Mol Cell Biomech. 5: 119-132.

McBeath R, et al. (2004) Cell shape, cytoskeletal tension, and RhoA regulate stem cell lineage commitment. Dev Cell. 6: 483-495.

McDevitt TC, et al. (2002) In vitro generation of differentiated cardiac myofibers on micropatterned laminin surfaces. J Biomed Mater Res. 60: 472-479.

McMahon JA, et al. (1998) Noggin-mediated antagonism of BMP signaling is required for growth and patterning of the neural tube and somite. Genes Dev. 12: 1438-1452.

Megeney LA, et al. (1996) bFGF and LIF signaling activates STAT3 in proliferating myoblasts. Dev Genet. 19: 139-145.

Mehra S, et al. (2004) A boolean algorithm for reconstructing the structure of regulatory networks. Metab Eng. 6: 326-339.

Meijer L and Raymond E. (2003) Roscovitine and other purines as kinase inhibitors. From starfish oocytes to clinical trials. Acc Chem Res. 36: 417-425.

Melendez-Vasquez CV, et al. (2001) Nodes of Ranvier form in association with ezrin-radixin-moesin (ERM)-positive Schwann cell processes. Proc Natl Acad Sci U S A. 98: 1235-1240.

Mendelsohn JD, et al. (2003) Rational design of cytophilic and cytophobic polyelectrolyte multilayer thin films. Biomacromolecules. 2003 4: 96-106.

Menendez L, et al. (2011) Wnt signaling and a Smad pathway blockade direct the differentiation of human pluripotent stem cells to multipotent neural crest cells. Proc Natl Acad Sci U S A. 108: 19240-19245.

Menn B, et al. (2010) Delayed treatment with systemic (S)-roscovitine provides neuroprotection and inhibits in vivo CDK5 activity increase in animal stroke models. PLoS One. 5: e12117.

Metzger SW, et al. (1999) Development and characterization of surface chemistries for microfabricated biosensors. J of Vacuum Sci & Tech a-Vacuum Surfaces and Films. 17: 2623-2628.

Meyer G and Nabil MA. (1988) Novel optical approach to atomic force microscopy. Applied Physics Letters. 53: 1045-1047.

Meyer T, et al. (2004) Micro-electrode arrays in cardiac safety pharmacology—A novel tool to study QT interval prolongation. Drug Saf. 27: 763-772.

Meyer T, et al. (2004b) QT-screen: high-throughput cardiac safety pharmacology by extracellular electrophysiology on primary cardiac myocytes. Assay Drug Dev Technol. 2: 507-514.

Miles GB, et al. (2004) Functional properties of motoneurons derived from mouse embryonic stem cells. J Neurosci. 24: 7848-7858.

Miller FD. (2007) Riding the waves: neural and nonneural origins for mesenchymal stem cells. Cell Stem Cell. 1: 129-130.

Miller SC, et al. (1988) Tumor necrosis factor inhibits human myogenesis in vitro. Mol Cell Biol. 8: 2295-2301.

Mitsumoto H, et al. (2001) Effects of cardiotrophin-1 (CT-1) in a mouse motor neuron disease. Muscle Nerve. 24: 769-777.

Mizuseki K, et al. (2003) Generation of neural crest-derived peripheral neurons and floor plate cells from mouse and primate embryonic stem cells. Proc Natl Acad Sci U S A. 100: 5828-5833.

Moe GK. (1962) On the multiple wavelet hypothesis of atrial fibrillation. Arch Int Pharmacodyn Ther. 183-188.

Mohammed JS, et al. (2004) Micropatterning of nanoengineered surfaces to study neuronal cell attachment in vitro. Biomacromolecules. 5: 1745-1755.

Mohan DK, et al. (2006) Toxin detection based on action potential shape analysis using a realistic mathematical model of differentiated NG108-15 cells. Biosens Bioelectron. 21: 1804-1811.

Mokry J, et al. (2007) Differentiation of neural stem cells into cells of oligodendroglial lineage. Acta Medica (Hradec Kralove). 50: 35-41.

Molnar P, et al. (2005) Biosurface Engineering. Encyclopedia of Medical Devices and Instrumentation. J.G. Webster. New York, John Wiley & Sons, Inc.

Molnar P, et al. (2007) Photolithographic Patterning of C2C12 Myotubes using Vitronectin as Growth Substrate in Serum-Free Medium. Biotechnol Prog. 23: 265-268.

Molnar P, et al. (2007b) Synaptic connectivity in engineered neuronal networks. Methods Mol Biol. 403: 165-173.

Molnar P, et al. (2007c) Modeling of action potential generation in NG108-15 cells. Methods Mol Biol. 403: 175-184.

Monaco EA 3rd and Vallano ML. (2005) Roscovitine triggers excitotoxicity in cultured granule neurons by enhancing glutamate release. Mol Pharmacol. 68: 1331-1342.

Monaco EA 3rd. (2004) Recent evidence regarding a role for CdkS dysregulation in Alzheimer's disease. Curr Alzheimer Res. 1: 33-38.

(56) References Cited

OTHER PUBLICATIONS

Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogenic differentiation. Development. 111: 741-748.
Morefield SI, et al. (2000) Drug evaluations using neuronal networks cultured on microelectrode arrays. Biosens Bioelectron. 15: 383-396.
Morganroth J and Gussak I. (2004) Cardiac Safety of Noncardiac Drugs: Practical Guidelines for Clinical Research and Drug Development. New York, Humana Press.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-1 mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIA1 Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-921.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Müller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481: 617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan To Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.

Nam Y, et al. (2006) Neural recording and stimulation of dissociated hippocampal cultures using microfabricated three-dimensional tip electrode array. J Neurosci Methods. 155: 296-299.
Nash MP, et al (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32: 4267-4274.
Natarajan A, et al. (2013) Engineered In Vitro Feed-Forward Networks. J Biotechnol Biomater. 3: 153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24: 1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(1-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci U S A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nyitrai G, et al. (2006) Extracellular level of GABA and Glu: in vivo microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.

(56) References Cited

OTHER PUBLICATIONS

O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 19-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helix-loop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1998) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclin-dependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Parker KK, et al. (2008) Myofibrillar architecture in engineered cardiac myocytes. Circ Res. 103: 340-342.
Parng C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicology. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteriod intervention in mdxmice. Muscle Nerve. 33: 66-77.
Peng HB, et al. (2003) Differential effects of neurotrophins and schwann cell-derived signals on neuronal survival/growth and synaptogenesis. J Neurosci. 23: 5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci U S A. 101: 12543-12548.
Peters A. (1964) Observations on the Connexions Between Myelin Sheaths and Glial Cells in the Optic Nerves of Young Rats. J Anat. 98: 125-134.
Peterson CA, et al. (1999) Effects of moisture on Fowler-Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithe muscle by chronic low frequency stimulation. J Muscle Res Cell Motil. 3: 215-221.
Pfeiffer SE, et al. (1993) The oligodendrocyte and its many cellular processes. Trends Cell Biol. 3: 191-197.
Pfrieger FW and Banes BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotropy. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90: 1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and McMorris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B-Chemical. 79: 115-126.
Rajnicek AM, et al. (1997) Contact guidance of CNS neurites on grooved quartz: influence of groove dimensions, neuronal age and cell type. J Cell Sci. 110: 2905-2913.

(56) References Cited

OTHER PUBLICATIONS

Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly(ethylene glycol) Photolithography to Create High-Density Cell Arrays on Glass. Langmuir. 19: 9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine)/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation in apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci U S A. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-1. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. J Neurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-641.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-119.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276: C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, al. et al (2005) Why drugs fail—a study on side effects in new chemical entities. Curr Pharm Des. 11: 3545-3559.
Schuster R and Holzhutter HG. (1995) Use of mathematical models for predicting the metabolic effect of large-scale enzyme activity alterations. Application to enzyme deficiencies of red blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote M and Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KATP channels integrated with creatine and adenylate kinases: amplification, tuning and sensing of energetic signals in the compartmentalized cellular environment. Mol Cell Biochem. 256-257: 243-256.

(56) References Cited

OTHER PUBLICATIONS

Selivanova OM, et al. (2003) Compact globular structure of Thermus thermophilus ribosomal protein S1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12: 1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor beta1a subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14: 1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19: 317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313: 107-117.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-1729.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.
Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2005) Molecular biology and genetics of Alzheimer's disease. C R Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 79.
Stenger DA, et al. (1992) Coplanar Molecular Assemblies of Aminoalkylsilane and Perfluorinated Alkylsilane -Characterization and Geometric Definition of Mammalian-Cell Adhesion and Growth. Journal of the American Chemical Society. 114: 8435-8442.
Stenger DA, et al. (1993) Surface determinants of neuronal survival and growth on self-assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.

(56) References Cited

OTHER PUBLICATIONS

Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison S and Mayne R. (1992) Formation of highly organized skeletal muscle fibers in vitro. Comparison with muscle development in vivo. J Cell Sci. 102: 643-652.
Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, al. et al (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. J Neurosci Res. 85: 47-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-903.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. nhibitors. Nat Rev Drug Discov. 2: 517-526.
Toga T, et al. (2007) The 5-HT(4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu K and Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J. 19: 1592-1601.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu AY. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-208.
Vakakis N, et al. (1995) In vitro myoblast to myotube transformations in the presence of leukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
van de Ven C, et al. (2007) The potential of umbilical cord blood multipotent stem cells for nonhematopoietic tissue and cell regeneration. Exp Hematol. 35: 1753-1765.
van der Valk J, et al. (2010) Optimization of chemically defined cell culture media—replacing fetal bovine serum in mammalian in vitro methods. Toxicol In Vitro. 24: 1053-1063.
van Rijen HV, et al. (2006) Connexins and cardiac arrhythmias. Adv Cardiol. 42: 150-160.
van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.

(56) References Cited

OTHER PUBLICATIONS

Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue culture: Effects on skeletal muscle organogenesis. In Vitro Cell Dev Biol. 24: 609-619.
Varghese K, et al. (2009) Regeneration and characterization of adult mouse hippocampal neurons in a defined in vitro system. J Neurosci Methods. 177: 51-59.
Varghese K, et al. (2010) A new target for amyloid beta toxicity validated by standard and high-throughput electrophysiology. PLoS One. 5: e8643.
Vargo TG, et al. (1992) Monolayer Chemical Lithography and Characterization of Fluoropolymer Films. Langmuir. 8: 130-134.
Vartanian T, et al. (1988) Oligodendrocyte substratum adhesion modulates expression of adenylate cyclase-linked receptors. Proc Natl Acad Sci U S A. 85: 939-943.
Ventimiglia R, et a. (1987) Localization of beta-adrenergic receptors on differentiated cells of the central nervous system in culture. Proc Natl Acad Sci U S A. 84: 5073-5077.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-L1 cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Z and Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J Neurochem. 101: 1172-1184.
Walsh K, al. et al (2005) Human central nervous system tissue culture: a historical review and examination of recent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and ciliary neurotrophic factor on the proliferation and differentiation of adult human myoblasts. Cell Mol Neurobiol. 28: 113-124.
Ward JH, et al. (2001) Micropatterning of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122: R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann N Y Acad Sci. 605: 1-14.
Wright CD, et al. (2008) Nuclear alpha1-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity in functional mammalian neuronal networks grown on patterned surfaces. J Neurosci Methods. 117: 123-131.
Xi J, et al. (2005) Self-assembled microdevices driven by muscle. Nat Mater. 4: 180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-1 transgenic rats. Transplantation. 82: 865-875.
Xu T, et al. (2004) Construction of high-density bacterial colony arrays and patterns by the ink jet method. Biotechnol Bioeng. 85: 29-33.
Xu T, et al. (2005) Inkjet printing of viable mammalian cells. Biomaterials. 26: 93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.

(56) References Cited

OTHER PUBLICATIONS

Yan J, et al. (2007) Extensive neuronal differentiation of human neural stem cell grafts in adult rat spinal cord. PLoS Med. 4: 318-332.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly(diol citrate) biodegradable elastomers. Biomaterials. 27: 1889-1898.
Yang L, et al. (2007) Increased asynchronous release and aberrant calcium channel activation in amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatterning capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatterning and its integration with micro/nanoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.
Zhou L, et al. (2005) Mechanistic model of cardiac energy metabolism predicts localization of glycolysis to cytosolic subdomain during ischemia. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.

\* cited by examiner

PATTERNED CARDIOMYOCYTE CULTURE ON MICROELECTRODE ARRAY

RELATED APPLICATION

This application claims priority from provisional application Ser. No. 61/257,504, filed on 3 Nov. 2009, which is incorporated herein by reference in its entirety.

STATEMENT OF GOVERNMENT RIGHTS

This invention was made with Government support under agency contract/grant number R01 EB005459 and K01 EB003465 awarded by the National Institutes of Health. The government has certain rights in this invention.

FIELD OF THE INVENTION

The present invention relates to the field of new drugs and, more particularly, to a patterned culture of cardiomyocytes formed on a multielectrode array and useful for in vitro testing for possible cardiac side effects by a new drug.

BACKGROUND OF THE INVENTION

The development of a high-throughput, high-information content device to study and understand cardiac electrophysiology would be important for the fields of cardiac physiology, tissue engineering and drug research. More than 850,000 people are hospitalized for arrhythmias each year and ventricular fibrillation (VF) is a leading cause of cardiac death[1]. Despite the intensive research in this area, the mechanism of VF is still poorly understood[2-5].

Arrhythmia is a known side effect of commercial drugs. One of the mechanisms by which drugs can cause a potentially fatal form of ventricular tachy arrhythmia, called Torsades de pointes (Tdp), is through the prolongation of the QT interval (in an ECG the length of the ventricular action potential). It has been reported that approximately 2-3% of all prescribed drugs can cause long QT syndrome[6, 7]. A broad range of cardiovascular drugs and antibiotics also have the potential risk of causing drug induced Tdp[8, 9]. At the same time, prolongation of the QT interval does not necessarily lead to Tdp; lengthening of the QT interval could even be antiarrhythmogenic, as it is considered a mechanism of action of the class III anti-arrhythmics[8, 9]. Thus, a relatively high-throughput method to identify cardiac side effects and differentiate between arrhythmic and anti-arrhythmic effects at an early stage of drug development would have a significant impact on the field.

Gap junctions play an important role in the propagation of excitation in cardiac tissue. Changes in gap junction function affect major cardiac parameters, such as conduction velocity (CV). It has been observed in several cardiovascular diseases that the expression of connexins (protein molecules that form gap junction channels) is decreased or their distribution is changed, leading to a malfunction in gap junction coupling [10]. Understanding the pharmacological modulation of cardiac gap junction channels would further aid the drug development enterprise.

Introduction of an in vitro method for cardiac side effect testing, which has high predictive value, would have a significant impact on drug development as it could also reduce the cost, time and the number of drugs failing in clinical trials[11]. in vitro testing would also reduce the need for animal testing and could be used to study drug effects with a functional assay, but at the cellular level. Other in vitro methods, such as whole heart experiments (Langendorff heart model) or the Purkinje fiber preparation are difficult and time consuming[11]. Traditional methods used to study QT interval prolongation at the cellular level include patch-clamp experiments. However, these experiments are time intensive, require a skilled operator and cannot be used to study action potential (AP) propagation or parameters such as CV and re-entry. Moreover, evidence suggests that prolongation of QT intervals is not the best predictor of Torsades de pointes. The measurement of the length, or the variability in the length, of the refractory period after a cardiac action potential may have more relevance for predicting arrhythmic behavior [9].

Cardiac myocytes cultured on microelectrode arrays (MEA) have several benefits compared to either traditional patch clamp electrophysiology or isolated organ methods. The use of MEAs in the investigation of cardiac side effects would provide information in a relatively high-throughput and low cost manner compared to standard patch-clamp electrophysiology. However, at this time, it is still a low information content method and this has limited its use. Cardiac myocytes on MEAs have been used in a number of studies to investigate the effect of toxins, such as pesticides[12] and cardioactive drugs[13] on cardiac field potentials. A commercial system has also been introduced to measure QT intervals in a relatively high-throughput fashion[14], but, to date, it has only limited applications. However, cardiac myocytes can now be maintained over longer periods of time[15], thus chronic experiments, such as the monitoring of network remodeling for specific diseases, is now feasible. In addition, serum-free formulations for cardiac culture have also been introduced, which would increase the reproducibility of such a system[16].

All of the above mentioned studies utilized unorganized monolayers of cardiomyocytes on the MEAs. Development of a patterned cardiac myocyte layer that is aligned with the electrodes of a MEA could solve several problems associated with the random spread of excitation in a cardiac monolayer, which makes evaluation of the obtained data, such as CV, difficult. It would also enable the development of specific open-loop or closed-loop stimulation protocols to measure critical parameters, such as the length of the refractory period after the action potential. It could also be used to create a high-throughput, low-cost functional reentry model.

There are several lines of evidence indicating that not only contact interaction with the surface but the shape of the attachment area determines the physiology of cardiac myocytes[17]. Pattern geometries determine the extent of the alignment/of the long axis of cardiac myocytes, alignment determines CV[18] and other physiological and pharmacological properties of cardiac tissues[19, 20].

Several different methods have been developed for cell patterning. One category of this technique is based on direct placement of cells or extracellular matrix molecules on desired locations and includes patterning through microfluidic channels[21-23], microcontact printing[24, 25] and inkjet printing[26]. Cardiac myocytes have previously been patterned on glass using photoresist[27] as well as other techniques[15, 17, 19, 20, 25]. Another method utilized photolithography following surface modification with self-assembled monolayers (SAMs) for neurons[28-30] as well as myocytes[15, 31]. The benefit of this method is the compatibility of the technique with cheap automated silicon manufacturing steps and the ability of the cells to self-assemble after random plating.

SAMs are one molecule thick monolayers attached to a surface composed of organic molecules, which have been extensively used for surface patterning[31-33]. Surface modification with SAMs is also compatible with advanced photolithography methods[30, 34]. Studies have also shown that cells survive on these surfaces for extended periods of time[35, 36], do not migrate off the patterned areas[34] and exhibit the typical morphology and physiology of the specific cell type[16, 37].

The goal of this study was the development of patterned, rat, cardiomyocyte cultures on MEAs in a serum-free medium for the study of cardiac physiology and pharmacology utilizing a high-throughput technique, but with high information content. An adsorbed fibronectin layer was used as the foreground because it supported cardiac myocyte attachment and growth and a 2-[Methoxy(Polyethyleneoxy) Propyl]TrimethoxySilane (SiPEG) SAM was used as the cell repellent background because of its excellent protein adsorption resistant properties[38]. The measurement of CV with the patterned cardiac myocyte monolayers and the feasibility to apply different stimulation protocols to the MEA/cardiac system was demonstrated. The action of 1-Heptanol and Sparfloxacin was also assessed. This method could easily be adapted for use with human cardiac myocytes to eliminate interspecies differences in drug side effect screening and could become an alternative to the existing more complex, expensive and time consuming methods.

SUMMARY OF THE INVENTION

With the foregoing in mind, the present invention advantageously provides a culture of patterned cardiomyocytes. The culture comprises a support substrate bearing a multi-electrode array and a negative surface resistant to cell attachment and deposited on the support substrate covering the multi-electrode array. The negative surface bears a pattern ablated thereon, preferably by laser photolithography. A positive surface promoting cell attachment is deposited on the pattern ablated on the negative surface and cardiomyocytes adherent to the positive surface and growing are aligned along the pattern.

Preferably, in the culture of patterned myocardiocytes the negative surface comprises a material selected from the group consisting of polyethylene glycol, polyacrylic acid and polyacrylamide. Most preferably, the material selected is polyethylene glycol and it is deposited essentially as a monolayer. The pattern on the negative surface is preferably ablated by laser lithography through a mask, as further explained below.

The positive surface preferably comprises a material selected from the group consisting of fibronectin, trimethoxysilylpropyldiethylenetriamine and pure glass.

In the culture described the cardiomyocytes are preferably of mammalian origin, and may be of neonatal rat Additionally, however, the cardiomyocytes may be derived from human embryonic stem cells.

The invention further includes a method of making the described culture of patterned myocardiocytes. The method comprises preparing a support substrate bearing a multi-electrode array, overlaying on the support substrate a negative surface resistant to cell adherence thereon, comprising polyethylene glycol and covering the multi-electrode array, ablating a pattern on the negative surface, depositing on the ablated pattern a positive surface promoting cell adherence thereon and including fibronectin, adhering cardiomyocytes on the positive surface, and culturing the cardiomyocytes so that they grow on the positive patterned surface and aligned therewith.

Yet additionally, the invention also includes an in vitro method of testing the effect of a compound on cardiac function. This method comprises providing patterned spontaneously beating cardiomyocytes according to the described culture. Recording a first electrical output from the cardiomyocytes. Contacting the cardiomyocytes with the compound being tested, Recording a second electrical output from the cardiomyocytes after being contacting with the compound. Finally, determining a change between the first and second electrical outputs as an indicator of altered cardiac function.

BRIEF DESCRIPTION OF THE DRAWINGS

Some of the features, advantages, and benefits of the present invention having been stated, others will become apparent as the description proceeds when taken in conjunction with the accompanying drawings. The drawings are presented solely for exemplary purposes and not with intent to limit the invention thereto. The following descriptions apply.

DETAILED DESCRIPTION OF THE PREFERRED EMBODIMENT

Figure 1:
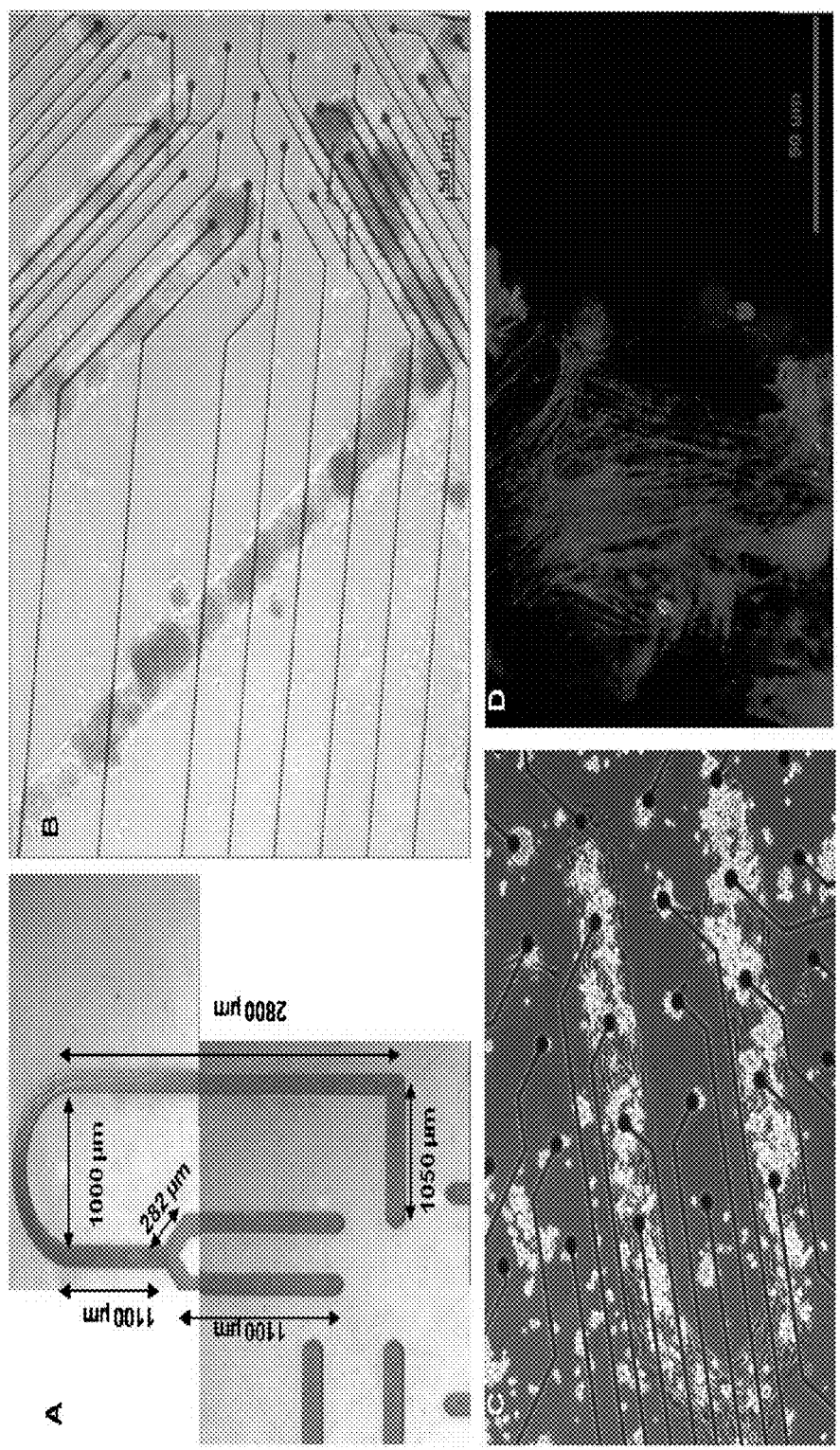
FIG. 1: Patterned neonatal cardiomyocytes. A: Pattern design and dimensions. B,C: Phase contrast pictures on day 12 of different regions of the pattern indicated in A. Field potentials measured at individual electrodes are marked in red in B. Electrode distance: 200 µm, D: Immunostaining with Rhodamine phalloidin for F-actin indicating cardiac myofibrils (note the visible striations). Nuclei are stained with DAPI (blue).

The present invention will now be described more fully hereinafter with reference to the accompanying drawings, in which preferred embodiments of the invention are shown.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical expressions given herein are intended to be approximate and not exact or critical figures unless expressly stated to the contrary. Accordingly, where appropriate to the invention and as understood by those of skill in the art, it is proper to describe the various aspects of the invention using approximate or relative terms and terms of degree commonly employed in the art, for example, so dimensioned, about, approximately, substantially, essentially, consisting essentially of, comprising, and effective amount.

Further, any publications, patent applications, patents, and other references mentioned herein are incorporated by reference in their entirety as if they were part of this specification. However, in case of conflict, the present specification, including any definitions, will control. In addition, the materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Other features, and advantages of the invention will be apparent from the following detailed description, and from the claims.

Materials and Methods
Surface Modification of Microelectrode Arrays with PEG Silanes MEAs containing 60, 10 μm diameter electrodes (Multichannel Systems, Germany) were cleaned by soaking the arrays in a detergent solution for 2 hours followed by sonication for 10 minutes. The arrays were then oxygen plasma cleaned for 20 minutes. Surface modification was completed by incubation of the MEAs in a 3 mM PEG silane, 2-[Methoxypoly(ethyleneoxy)propyl]trimethoxysilane (MW=460-590, Gelest), solution in toluene, with 37% concentrated HCL added to achieve a final value of 0.08% (0.8 ml HCL/L), for 45 minutes at room temperature. The arrays were then rinsed once in toluene, twice in ethanol, twice in water and sonicated in water for 2 minutes to remove the non-covalently linked material[39]. The arrays were air dried with nitrogen and stored in a dessicator overnight.

Laser Ablation and Patterning of the Microelectrode Arrays

The MEAs were patterned by laser ablation photolithography using a deep UV (193 nm) excimer laser (Lambda Physik) at a pulse power of 230 mW and a frequency of 10 Hz for 45 seconds through a quartz photomask (Bandwidth foundry, Eveleigh, Australia). The arrays were sterilized using 70% isopropanol and then incubated with 5 μg/ml of fibronectin in a Phosphate buffered solution (Invitrogen) for 20 minutes at room temperature. The solution was removed and the surface was first rinsed with PBS, followed by the plating medium, and then dried before the cells were plated.

Neonatal Rat Cardiomyocyte Culture

The neonatal rat cardiomyocyte culture was prepared using the cardiac isolation kit from Worthington[40]. All animal work was approved by the UCF IACUC and followed NIH guidelines. Briefly, two day-old rat pups were euthanized in a precharged $CO_2$ chamber. Hearts were dissected and minced in ice cold Hanks balanced salt solution (HBSS). Cardiac myocytes were dissociated by incubation of the hearts in trypsin (100 μg/ml in HBSS) for 16 hours at 2-8° C. The hearts in the trypsin solution were briefly warmed with a trypsin inhibitor before adding collegenase (300 units/ml in L-15 medium) for 45 minutes in a water bath at 37° C. followed by mechanical trituration. The cell solution was filtered to remove any remaining tissue and centrifuged at 50 g for 5 minutes at 22° C. The cells were resuspended in high glucose Dulbecco's modified eagle medium (DMEM, Gibco/Invitrogen) supplemented with 10 ml Fetal Bovine Serum (Gibco/Invitrogen) and 1 ml penicillin streptomycin (Gibco/Invitrogen), preplated in Petri dishes and incubated at 37° C. and in 5% $CO_2$ for 45 minutes. This was necessary to eliminate the fibroblasts. The supernatant from the Petri dishes was centrifuged at 50 g for 5 min at 22° C. The cells were then resuspended in the plating medium. The serum-free plating medium consisted of: 100 ml Ultraculture medium (Bio Whittaker Cambrex) supplemented with 10 ml B27, 1 ml L-glutamine (Gibco/Invitrogen), 1 ml Penicillin Streptomycin, 0.375 g dextrose (Fisher Scientific) in 800 μl water, 1 ml non-essential amino acids and 1 ml of Hepes buffer (Gibco/Invitrogen)[41]. Additional growth factors were also added to improve cell survival in the serum-free conditions. They included 0.1 μg/ml of L-thyroxine, 10 ng/ml of Epidermal growth factor (Sigma-aldrich) and 0.5 μg/ml of Hydrocortisone (BD biosciences). Cells were plated at a density of 1000 cells/$mm^2$ on the MEAs. The medium was changed 24 hours after plating. Subsequent changing of the medium was performed every third day.

Immunostaining

Patterned Cardiomyocytes were immunostained for F-Actin with Rhodamine Phalloidin (Invitrogen, R415), using a protocol provided by the company. Briefly, the cells were washed with PBS and fixed using 3% Formaldehyde. The coverslips were extracted with 0.1 ml Triton X®. The staining solution (with 1% Bovine Serum Albumin to prevent background staining) was added at a dilution of 1:40 in PBS and coverslips were incubated for 30 minutes. Imaging was done using confocal microscopy.

Multielectrode Extracellular Recordings

The cardiac myocytes were cultured on patterned metal MEAs (Planar 10 μm electrodes, 200 μm separation, Multichannel-systems). A 60 channel amplifier (MEA1040, Multichannel-systems) was used to record electrical activity from the spontaneously beating cardiac cells. The same electrodes were also used for stimulation utilizing a stimulus generator (STG 1002, Multichannel systems). The cells were stimulated utilizing 500 mV, 1 ms wide bipolar pulses at 2 Hz. The recording medium was the same as the plating medium with the pH adjusted to 7.3 using HEPES buffer. After a 30 minute incubation period, APs were detected and recorded using built in functions of the Multichannel System software. For drug experiments, 50 µM 1-Heptanol (Gibco/Invitrogen) was added to the bathing medium and recordings were performed before and 15 minutes after drug administration with additional recordings done at 15 minute intervals. For Sparfloxacin (Sigma-Aldrich), 2 µM of the drug was added to the recording medium and recordings were taken in 15 minute intervals before and after drug administration. The data was further analyzed using software written using Matlab and Clampfit (Axon Instruments).

Results

Surface Modification of the Microelectrode Arrays

Our laboratory routinely uses SAMs to modify and pattern glass coverslips for cell culture applications[15, 16, 30-32, 42]. However, patterning cardiac myocytes on MEAs presented a challenge for three primary reasons: 1) The complex composition of the MEA surface made the verification of the surface modification step difficult, 2) MEAs are expensive, thus methods needed to be developed that enabled them to be cleaned and refunctionalized for repeated use and 3) patterned cardiac myocytes do not grow optimally on the standard trimethoxysilylpropyldiethylenetriamine (DETA) surfaces[15] nor on clean glass. Thus, a cell resistant background surface was needed which was also resistant to protein adsorption as this would allow fibronectin incubation on the foreground and prevent its adherence to the background, enabling cardiac myocyte attachment. Thus, poly(ethylene glycol). (PEG) was chosen for the background because of its excellent protein adsorption resistance. X-ray Photoelectron Spectroscopy (XPS) and contact angle measurements were used to analyze the results of the surface modifications and throughout the entire study for quality assurance purposes.

Cultured Neonatal Rat Cardiomyocytes on Patterned Surfaces in Serum-Free Medium

The growth and activity of neonatal rat cardiomyocytes on the patterned MEAs were assessed for over 2 weeks. The cells attached to the fibronectin, but not to the PEG background and showed clearly delineated regions (FIG. 1). This allowed the beating cells to grow exclusively over specific electrodes. The cells formed monolayers by day 2 and spontaneous contraction and beating activity began on day 4 and was consistent throughout the pattern. Cell survival and activity improved markedly with the addition of L-thyroxine, Epidermal growth factor and Hydrocortisone to the culture medium as indicated in the Methods. In a previous publication cells were shown to maintain spontaneous beating actively for up to 2 months in vitro [15]. Additionally, and by way of prophetic example, we believe the cardiomyocytes used in the invention could be derived from human embryonic stem cells (HESCs).

Extracellular Recordings from Patterned Cardiomyocytes on the MEAs

The electrical activity of the spontaneously contracting cells patterned on the microelectrodes was extracellularly recorded using the MEA system. Cardiac myocytes formed a morphologically homogenous, aligned, integrated network of cells that communicated through gap junctions and displayed normal tissue electrophysiology. The recorded field potential (FP) signals correlated with the contraction cycle.

Figure 2:
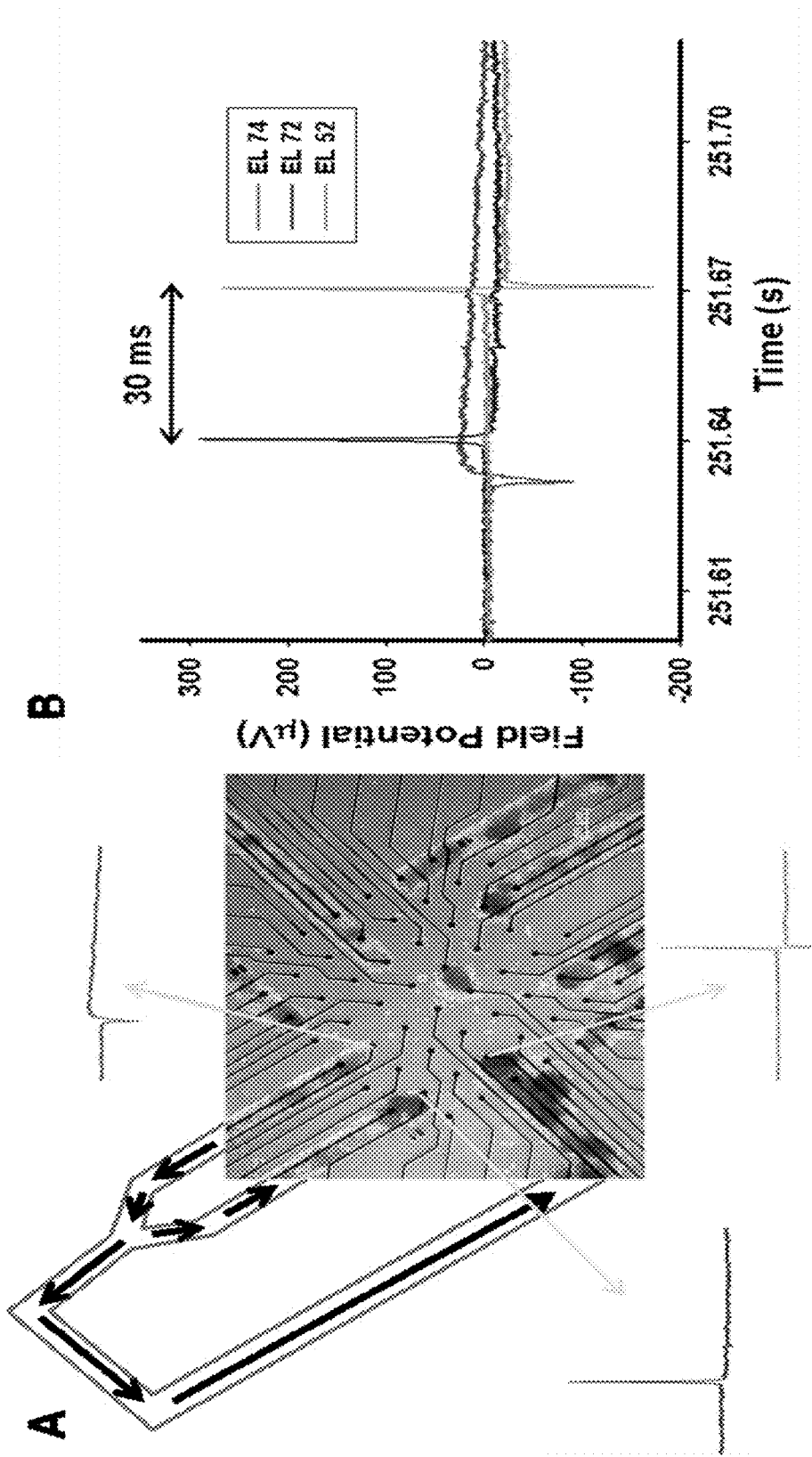
FIG. 2: Action potential (AP) conduction in patterned cardiac myocyte monolayers. A: phase contrast picture of cardiac myocyte patterns on the top of the substrate embedded electrodes (electrode distance is 200 µm) with a sketch of the conduction pathway on the completed pattern and with the recorded extracellular signals on the given electrodes. B: Overlay of the recorded traces showing the temporal relationship of the signals. A spontaneous AP was generated in the cardiac myocyte monolayer in the right fork of the pattern, close to electrode 74. This AP spread through the pattern reaching electrode 74 first, electrode 72 second and with a much longer delay (due to the longer path) electrode 52 last. Conduction velocity (CV) was determined based on the time delay in the signal between electrode 74 and 52 and the known pattern geometry. The calculated CV in this experiment was 0.190.

In random cultures the direction and speed of the propagation of excitation (action potentials) have been shown to depend on a number of variables, including intercellular resistance across the gap junctions and the depolarizing sodium current[43-45]. For extracellular MEA recordings, previous research had indicated that the excitation wave could be followed through the monolayer as the increasing delay in field potential peak times and could be used to determine the pathway of the excitation as it moved away from the initiation site[46]. However, a direct determination of the CV has been difficult in unpatterned monolayers, even though the timing of FP generation could be estimated. With patterning of the cells on the electrode array, the exact path of a spontaneous excitation wave can be determined and then, using the path length, conduction velocity can be calculated with a high degree of accuracy. Moreover, because of the pre-determined pathway, there is no need to image the wave propagation, just the measurement of the start and end times of the waves on the patterns as recorded by the microelectrodes in the array. Thus, in later high-throughput applications significantly fewer electrodes would be necessary for these measurements and imaging would not be a necessary requirement for analysis. FIG. 2 shows a typical recording and the method for the determination of propagation direction. FIG. 2B emphasizes the delay between FPs at different electrodes on the pattern, which enabled the determination of CV with high temporal resolution. The signal propagation was also visualized using an Imaging software routine written in Matlab 6.5[47]. The program converted recordings from the electrodes into a video indicating the field potential movement across an 8×8 grid. Snapshots from the video are shown in the supplementary data. This program also verified the origin of the excitation wave and confirmed our CV results obtained using the earlier method (FIG. 2.).

The conduction velocity was calculated to be 0.190±0.025 m/s for spontaneous firing of the patterned cardiomyocytes over eight different MEAs. Previous research has shown that in vitro conduction velocities ranged from 0.12 m/s[48] to 0.242 m/s[49]. In a computer simulation of AP propagation in cardiac fibers in realistic conditions (taking into account extracellular solutions and spaces) the conduction velocity was 0.504 m/s[50]. In the human heart the AP generated by the Sino-atrial node spreads through the atria at a conduction velocity of 0.5 m/sec[51].

Figure 3:
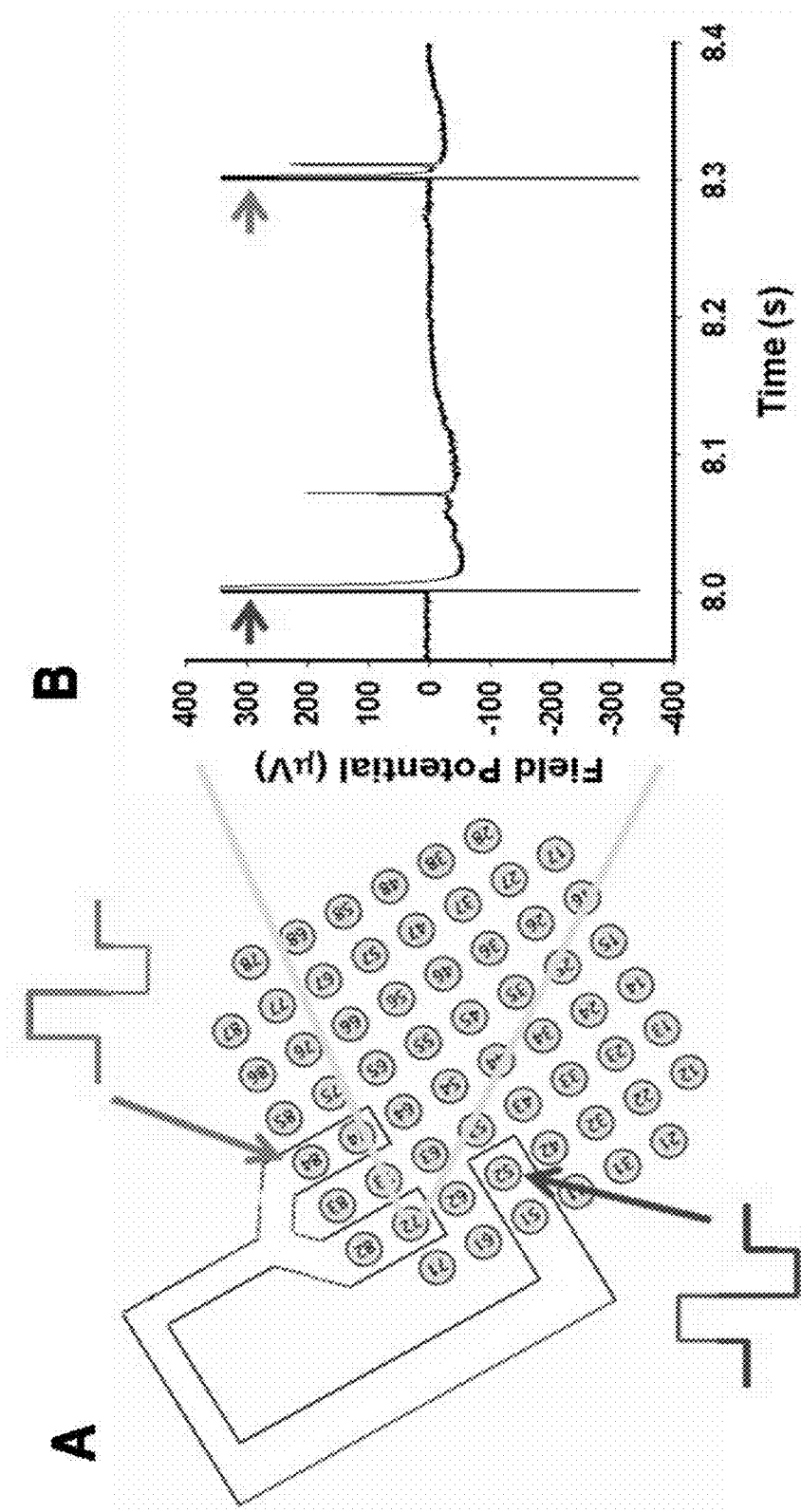
FIG. 3: Measurement of conduction velocity in patterned cardiac myocyte monolayers with electrical stimulation. A: Electrodes 52 and 84 were stimulated alternatively with a time delay of 300 ms and the response was recorded at electrode 72. B: E72 exhibited both long and short time delays in FP generation based on the distance the AP had to travel from the stimulation site.

The conduction velocity on patterned cardiac monoloyers was also measured with stimulation. In these experiments, the cardiac pattern was stimulated at the two ends of the pattern, over a distance of 0.77 mm with 1 ms wide bipolar pulses with an amplitude of 500 mV at a frequency of 2 to 4 Hz (FIG. 3). The conduction velocity at 2 Hz stimulation was calculated to be 0.315±0.011 m/s (n=8). Previous research has indicated that rapid electrical stimulation in cultured, neonatal rat cardiomyocytes had an effect on the expression of Connexin [43] leading to changes in conduction properties[52], including an increase in conduction velocity.

This study showed that rapid electrical stimulation caused an increase in conduction velocity compared to the non-stimulated or spontaneous case. These results also indicated that accurate estimation of conduction velocity and propagation path could be determined in both the stimulated and in the spontaneous case. The measurement of the frequency dependence of conduction velocity could help in the understanding of the electrophysiological properties of cultured, neonatal rat cardiac myocytes, and ultimately, the physiology and pharmacology of the heart. The stimulated conduction velocity was also closer to the modeled values in the literature as well as to those generated by the SA node in the heart in vivo.

Electrical stimulation optimization experiments and measurement of refractory period after the AP The stimulation protocol was optimized by determining a minimal threshold which reliably generated contraction from the cells. The cardiomyocytes were stimulated with 2 Hz, 500 mV, 1 ms wide bidirectional pulses at different electrodes. As seen in FIG. 3, the time-delay between the stimulation artifact and the FP at the different electrodes is in good correlation with the distance between the stimulation and recording electrodes. The excitation wave spread evenly on branched patterns as evidenced by the zero time difference at the end of the branches.

Figure 4:
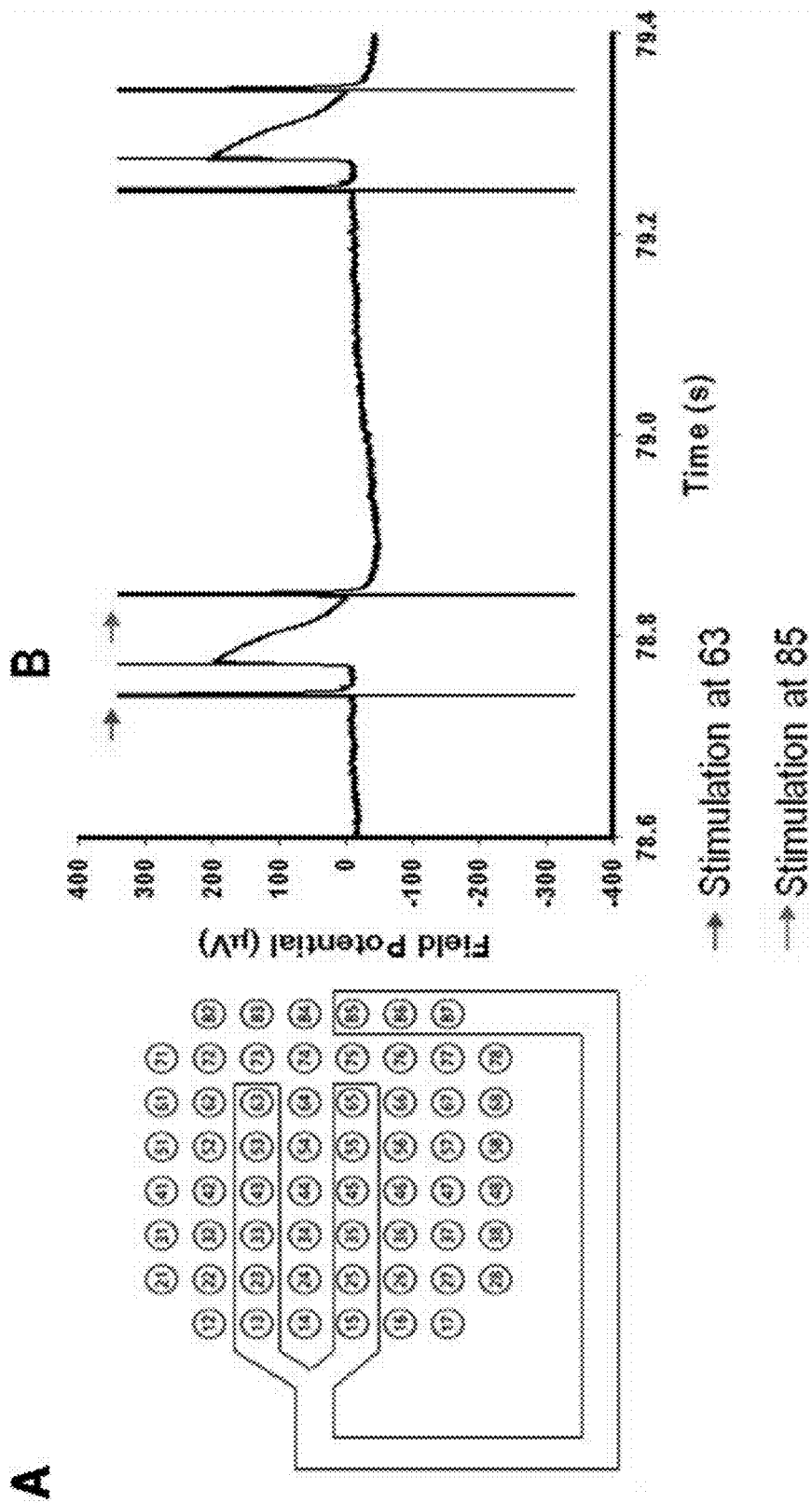
FIG. 4: Measurement of refractory period after cardiac action potential. Electrodes 63 and 85 (see pattern geometries on the left) were stimulated alternatively according to the following protocol: E63, 100 ms delay, E85, 400 ms delay, E63 again. Right panel shows recording at electrode 87. Stimulating E85 100 ms after the stimulation of E63 failed to evoke an AP because this delay was too short, cells were stimulated in their refractory period. By chance, cell electrode coupling on electrode E85 was especially strong in this experiment, thus the extracellular recording approximately replicated the shape of the intracellular AP illustrating the relationship of the AP and the stimulation. When the stimulation delay between E63 and E85 was 250 ms, both stimulations evoked an action potential at electrode 87.

As shown in FIG. 4, paired pulse stimulation protocols could also be used with the defined cardiac patterns. By varying the time-delay between stimulations the absolute/relative refractory period after AP generation could be mapped (FIG. 4). If the stimulation delay between the two electrodes was too short, the second stimulus failed to evoke a second propagating AP. This experiment suggests new possibilities to study phenomena difficult to measure in random (not constrained) monolayers, such as re-entry, the refractory period after an AP and arrhythmia.

Pharmacology and Toxin Studies

One of the most important applications of this system could be the measurement of the effect of drugs and toxins on cardiac function. Two pharmacological agents, 1-Heptanol and Sparfloxacin, were tested to demonstrate the usability of this system for pharmacological and toxicology studies.

Figure 5:
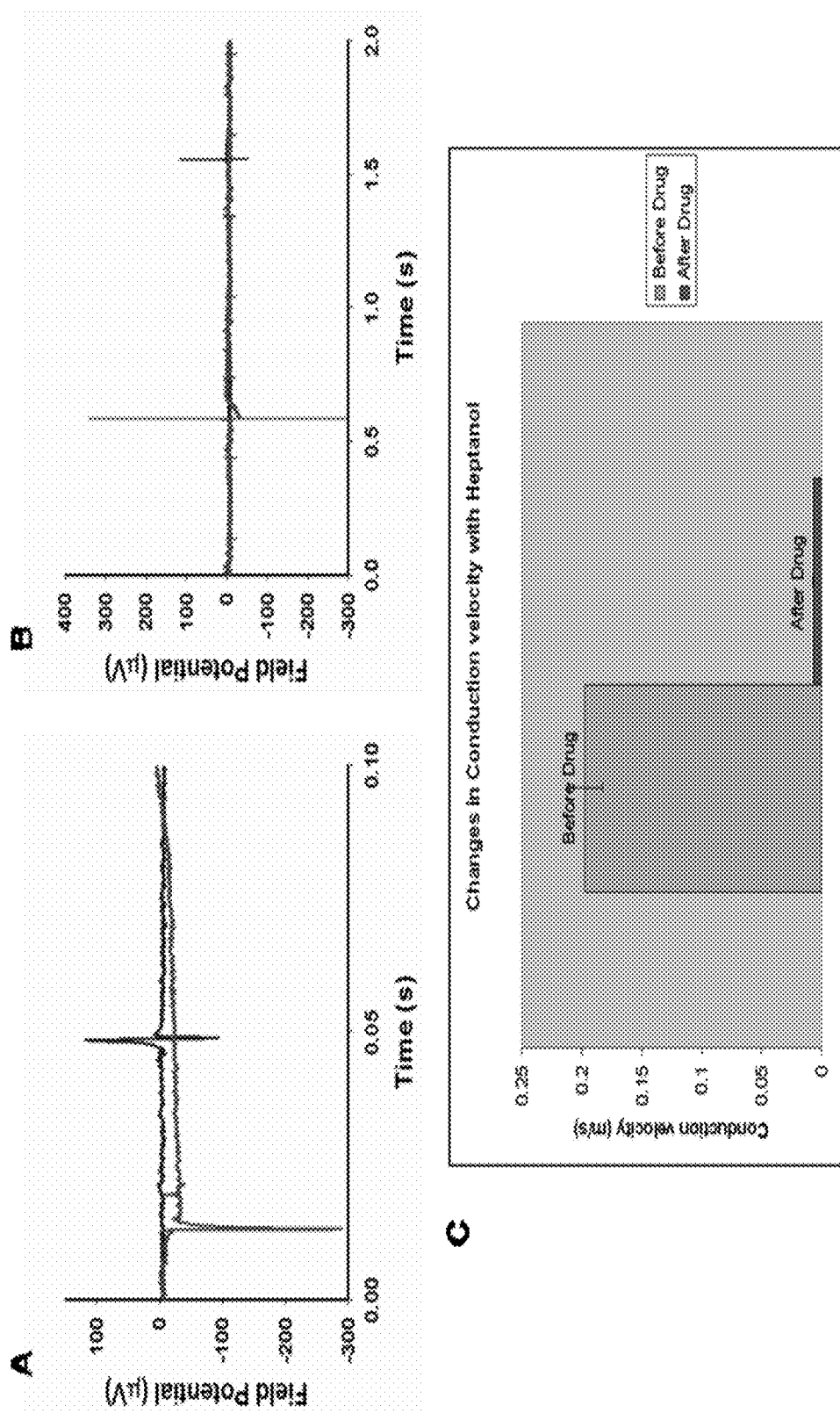
FIG. 5: Effect of the gap junction blocker 1-Heptanol. A: Propagation of excitation between the two end points in the pattern (Electrodes 84 and 52) before addition of the drug. The CV was measured to be 0.197 m/sec B: Propagation of excitation after the drug. The CV was calculated as 0.0066 m/sec. The drug effect on the CV measured over 4 MEAs.
Figure 6:
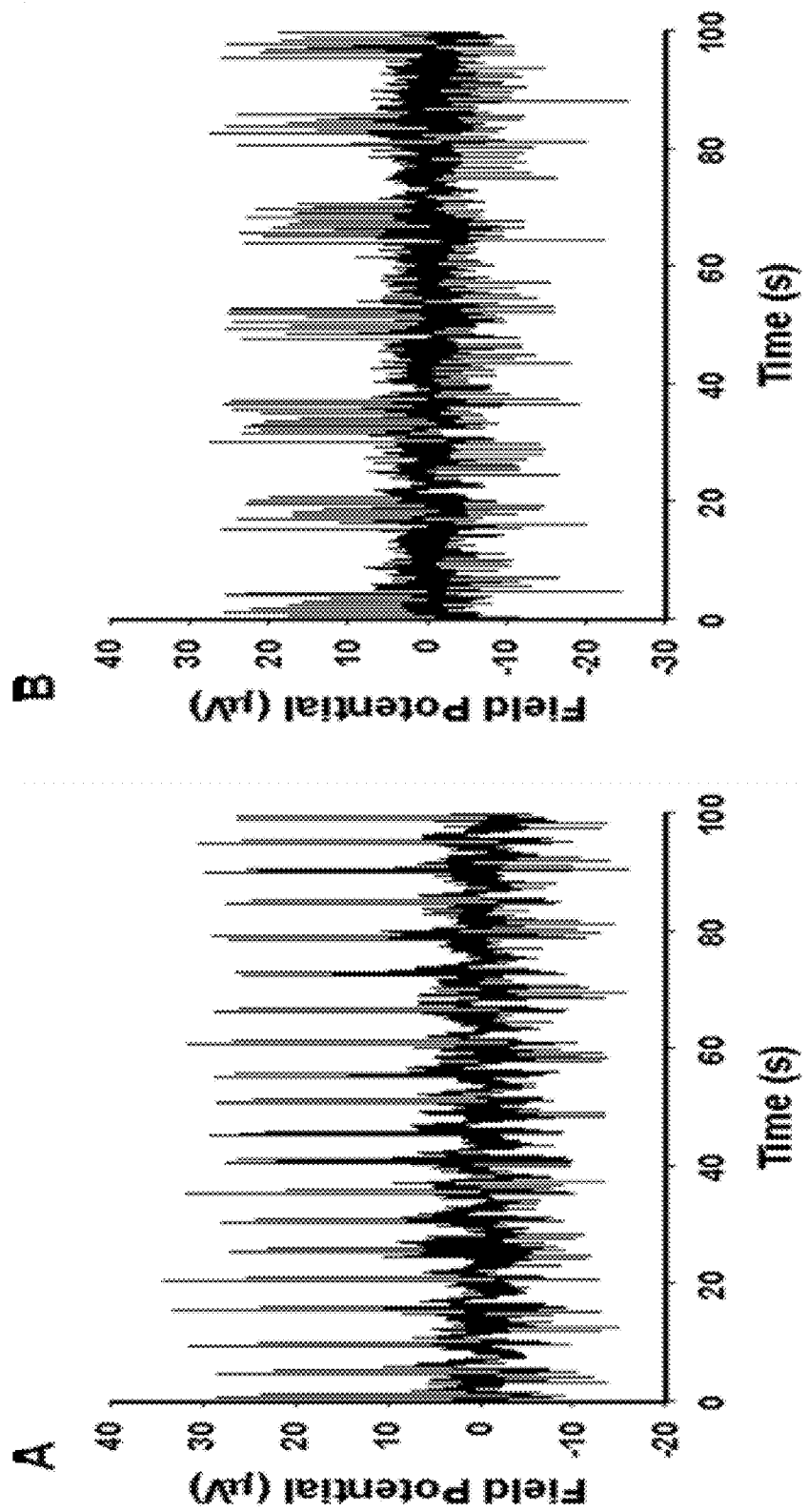
FIG. 6: Effect of the HERG channel antagonist Sparfloxacin. A: Field potential recordings before addition of Sparfloxacin indicated stable beating frequencies and synchronous activity B: Field potential recording after the addition of 2 μM Sparfloxacin showed burst like activity with higher intra-burst frequencies and no synchrony between electrodes.

Patterned spontaneously beating cardiomyocytes were exposed to 50 µM 1-Heptanol in the recording medium and the FPs were recorded at 15 minute intervals. A control recording was taken before the toxin application. As shown in FIG. 5, 1-Heptanol had a marked effect on the time for propagation of the excitation wave; it significantly increased the value measured before treatment. The increase in the time delay indicates a block and uncoupling of the gap junctions and delays the FP between the two recording electrodes. The CV was calculated to be 0.0066±0.0004 (n=4), a significant decrease from 0.197±0.014 m/s (n=4), and this result clearly shows that the effect of a gap junction blocker can be analyzed using this system.

Effect of Sparfloxacin

Sparfloxacin is a fluoroquinone antibiotic and HERG channel antagonist that is known to cause QT prolongation, Tdp and ventricular fibrillation[13, 53]. Application of 2 µM of Sparfloxacin to the recording medium caused a significant change in the spontaneous beating frequency within 25 minutes, with an increased FP length, non-synchronous contractions similar to fibrillation and burst-like beating activity as shown in FIG. 5. The beating frequency changed from a stable value of 0.6 Hz-1 Hz to intra-bursts with a higher frequency range of 1 Hz-1.2 Hz. The loss of synchrony between the electrodes measured also indicated a propagation block in the monolayer.

Discussion

Surface Modification, Photolithographic Patterning and Patterned Cardiac Myocyte Cultures on Microelectrode Arrays In this study, we have shown that the surface of commercial multielectrode arrays could be functionalized with SiPEG self-assembled monolayers. The PEG layer may be ablated and subsequently patterned using photolithographical techniques and that incubation of the patterns with 5 µg/ml fibronectin for 20 minutes did not affect the cell resistive properties of PEG, but significantly improved the attachment of cardiac cells to the glass surface. Surface analysis of the MEAs after modification indicated that both PEG-Silane modification and fibronectin adsorption on the ablated areas of the MEA surface was successful. The patterned commercial electrodes were reusable 6-10 times without observable decline in the quality of electrophysiological recordings. Rat neonatal cardiac myocytes demonstrated normal physiology and formed beating monolayers on the areas designated by the patterns.

Manipulating cells, determining their attachment, growth and differentiation in cultures has became important in applications such as tissue engineering, toxin detection, drug screening and robotics. Unfortunately, there is no generally applicable method to pattern all cell types. The method developed here using a protein adsorption resistant background, SiPEG, followed by protein adsorption (fibronectin) to the ablated area is a relatively simple, fast and inexpensive solution for this problem and could be generalized for 'difficult to pattern' cells.

Electrophysiology, Toxin and Drug Effects

The patterned cells formed a confluent, aligned and interconnected network of spontaneously contracting cells communicating via gap junctions. The activity of the cells could be measured using the MEA. The extracellular electrodes allowed not only recording, but also stimulation of the patterned cardiac myocyte monolayers. For the measurement of conduction velocity three different methods were used: 1) traditional video-monitoring of the excitation wave in the monolayer, 2) measurement of the speed of the spontaneous excitation waves on the patterns via the MEA and 3) measurement of the propagation of a stimulation-evoked extracellular field potential. All of these methods produced consistent results which were in reasonable agreement with published in vivo data. Conduction velocity increased with rapid electrical stimulation indicating that cardiac cell physiology can be studied using this method. Also, it was seen that the variability of the CV measurements decreased from about 15% as seen with the recordings from spontaneous APs to about 5% with stimulated APs. Patterning of the monolayers made CV measurements simpler, faster and more reliable. In future commercial applications this may be a more cost effective and a higher throughput technique for screening the cardiac side effects of drug candidates as it also eliminates the need for imaging of the propagation waves in the system. Patterning would also drastically reduce the number of required electrodes.

We have also demonstrated that alternating stimulation at different electrodes on the patterns could be used to measure the refractory period after APs, an important parameter for determining potentially fatal pharmacological side effects. This technique could also be a valuable tool for the study of cardiac defects, such as reentrant arrhythmia. Further development of this technology, especially for use with human cells, could significantly affect pharmaceutical drug development enabling high information content cardiac side effect screening.

Two pharmacological agents, 1-Heptanol and Sparfloxacin, were used to demonstrate the effectiveness of this method for drug screening. Both of these compounds are known to have cardiac side effects. 1-Heptanol is a gap junction blocker, whereas Sparfloxacin is an antibiotic that was taken off the market due to cardiac side effects. Our results were in agreement with the literature as 1-Heptanol drastically decreased the CV in the cardiac myocyte monolayers without completely blocking the conduction, whereas Sparfloxacin caused fibrillations which initiated a complete conduction block. These results indicated that specific drug actions can be studied using this system. 1-Heptanol affected the conduction velocity properties, while maintaining the synchronicity of the beating cells. The addition of Sparfloxacin to the cells caused a loss in rhythmicity resulting in a burst-like activity similar to fibrillations that are shown to have occurred in animal and human trials for the drug. These promising initial results support the need for further development of this system as a high-throughput, high-information content functional drug screening platform.

CONCLUSION

A simple and reliable method for patterning cardiac myocytes on multielectrode arrays has been disclosed. This method is compatible with 1.5 standard silicon manufacturing steps. Patterning of the cardiac myocytes increased the information content of the traditional multielectrode array recordings by enabling measurement of CV in a fast and simple way. Moreover, using paired stimulation, the measurement of the refractory period after the action potentials became possible. Measurement of the effect of drugs with known cardiac effects, was in agreement with the literature. Further development of this method could result in cheaper, faster, pharmaceutical side-effect screening with higher predictive value.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Jackson J Ht, Frech F, Ronen R, Mullany L, Lennert B, Jhaveri V. Assessment of drug therapy management and the prevalence of heart failure in a managed care population with hypertension. J Manag Care Pharm 2004; 10(6):513-520.
2. Lin J W, Garber L, Qi Y R, Chang M G, Cysyk J, Tung L. Region [corrected] of slowed conduction acts as core for spiral wave reentry in cardiac cell monolayers. Am J Physiol Heart Circ Physiol 2008; 94(1):H58-65.
3. Moe G K. On the multiple wavelet hypothesis of atrial fibrillation. Arch Int Pharmacodyn Ther 1962; (140):183-188.
4. Nash M P, Mourad A, Clayton R H, Sutton P M, Bradley C P, Hayward M, et al. Evidence for multiple mechanisms in human ventricular fibrillation. Circulation 2006; 114(6): 536-542.
5. Pijnappels D A, van Tuyn J, de Vries A A, Grauss R W, van der Laarse A, Ypey D L, et al. Resynchronization of separated rat cardiomyocyte fields with genetically modified human ventricular scar fibroblasts. Circulation 2007; 116 (18):2018-2028.
6. Recanatini M, Poluzzi E, Masetti M, Cavalli A, De Ponti F. QT prolongation through hERG K(+) channel blockade: current knowledge and strategies for the early prediction during drug development. Med Res Rev 2005; 25(2):133-166.
7. Sala M, Lazzaretti M, De Vidovich G, Caverzasi E, Barale F, d'Allio G, et al. Electrophysiological changes of cardiac function during antidepressant treatment. Ther Adv Cardiovasc Dis 2009; 3(1):29-43.
8. Campbell T J, Williams K M. Therapeutic drug monitoring: antiarrhythmic drugs. Br J Clin Pharmacol 2001; 52 Suppl 1:21 S-34S.
9. Hondeghem L M. Relative contributions of TRIaD and QT to proarrhythmia. J Cardiovasc Electrophysiol 2007; 18(6):655-657.
10. van Rijen H V, van Veen T A, Gros D, Wilders R, de Bakker J M. Connexins and cardiac arrhythmias. Adv Cardiol 2006; 42:150-160.
11. Suter W. Predictive value of in vitro safety studies. Curr Opin Chem Biol 2006; 10(4):362-366.
12. Natarajan A, Molnar P, Sieverdes K, Jamshidi A, Hickman J J. Microelectrode array recordings of cardiac action potentials as a high throughput method to evaluate pesticide toxicity. Toxicol in vitro 2006; 20(3):375-381.
13. Reppel M, Igelmund P, Egert U, Juchelka F, Hescheler J, Drobinskaya I. Effect of cardioactive drugs on action potential generation and propagation in embryonic stem cell-derived cardiomyocytes. Cell Physiol Biochem 2007; 19(5-6):213-224.
14. Meyer T, Boven K H, Gunther E, Fejtl M. Micro-electrode arrays in cardiac safety pharmacology: a novel tool to study QT interval prolongation. Drug Saf 2004; 27(11):763-772.
15. Dhir V, Natarajan A, Stancescu M, Chunder A, Bhargava N, Das M, et al. Patterning of diverse mammalian cell types in serum free medium with photoablation. Biotechnol Prog 2009; 25(2):594-603.
16. Das M, Molnar P, Gregory C, Riedel L, Hickman J J. Long-term Culture Of Embryonic Rat Cardiomyocytes on an Organosilane Surface in a Serum Free Medium. Biomaterials 2004; 25(25):5643-5647.
17. Parker K K, Tan J, Chen C S, Tung L. Myofibrillar architecture in engineered cardiac myocytes. Circ Res 2008; 103(4):340-342.
18. Bourgeois E B, Fast V G, Collins R L, Gladden J D, Rogers J M. Change in Conduction Velocity due to Fiber Curvature in Cultured Neonatal Rat Ventricular Myocytes. Ieee Trans Biomed Eng 2009; 56(3):855-861.
19. Badie N, Satterwhite L, Bursac N. A Method to Replicate the Microstructure of Heart Tissue in vitro Using DTMRI-Based Cell Micropatterning. Ann Biomed Eng 2009; 37(12):2510-2521.
20. Kaji H, Takii Y, Nishizawa M, Matsue T. Pharmacological characterization of micropatterned cardiac myocytes. Biomaterials 2003; 24(23):4239-4244.
21. Andersson H, van den Berg A. Microfabrication and microfluidics for tissue engineering: state of the art and future opportunities. Lab Chip 2004; 4(2):98-103.
22. Khademhosseini A, Bettinger C, Karp J M, Yeh J, Ling Y, Borenstein J, et al. Interplay of biomaterials and microscale technologies for advancing biomedical applications. J Biomater Sci Polym Ed 2006; 17(11):1221-1240.
23. Morin F, Nishimura N, Griscom L, Lepioufle B, Fujita H, Takamura Y, et al. Constraining the connectivity of neuronal networks cultured on microelectrode arrays with microfluidic techniques: a step towards neuron-based functional chips. Biosens Bioelectron 2006; 21(7); 1093-1100.
24. Kane R S, Takayama S, Ostuni E, Ingber D E, Whitesides G M. Patterning proteins and cells using soft lithography. Biomaterials 1999; 20(23-24):2363-2376.
25. McDevitt T C, Angello J C, Whitney M L, Reinecke H, Hauschka S D, Murry C E, et al. in vitro generation of differentiated cardiac myofibers on micropatterned laminin surfaces. J Biomed Mater Res 2002; 60(3):472-479.
26. Xu T, Gregory C A, Molnar P, Cui X, Jalota S, Bhaduri S B, et al. Viability and electrophysiology of neural cell structures generated by the inkjet printing method. Biomaterials 2006; 27(19):3580-3588.

27. Rohr S, Scholly D M, Kleber A G. Patterned growth of neonatal rat heart cells in culture. Morphological and electrophysiological characterization. Circ Res 1991; 68:114-130.
28. Hickman J J, Bhatia, S. K., Quong, J. N., Shoen, P., Stenger, D. A., Pike, C. J. and Cotman, C. W. Rational pattern design for in vitro cellular networks using surface photochemistry. J Vac Sci Technol A 1994; 12:607-616.
29. Kleinfeld D, Kahler K H, Hockberger P E. Controlled outgrowth of dissociated neurons on patterned substrates. J Neurosci 1988; 8(11):4098-4120.
30. Ravenscroft M S, Bateman K E, Shaffer K M, Schessler H M, Jung D R, Schneider T W, et al. Developmental neurobiology implications from fabrication and analysis of hippocampal neuronal networks on patterned silane-modified surfaces. J Am Chem Soc 1998; 120(47):12169-12177.
31. Molnar P, Wang W, Natarajan A, Rumsey J W, Hickman J J. Photolithographic patterning of C2C12 myotubes using vitronectin as growth substrate in serum-free medium. Biotechnol Prog 2007; 23(1):265-268.
32. Rumsey J W, Das M, Bhalkikar A, Stancescu M, Hickman J J. Tissue engineering the mechanosensory circuit of the stretch reflex arc: sensory neuron innervation of intrafusal muscle fibers. Biomaterials 2010; 31:8218-8227.
33. Stenger D A, Georger J H, Dulcey C S, Hickman J J, Rudolph A S, Nielsen T B, et al. Coplanar Molecular Assemblies of Aminoalkylsilane and Perfluorinated Alkylsilane—Characterization and Geometric Definition of Mammalian-Cell Adhesion and Growth. J Am Chem Soc 1992; 114(22):8435-8442.
34. Corey J M, Wheeler B C, Brewer G J. Compliance of hippocampal neurons to patterned substrate networks. J Neurosci Res 1991; 30(2):300-307.
35. Das M, Bhargava N, Bhalkikar A, Kang J-F, Hickman J J. Temporal neurotransmitter conditioning restores the functional activity of adult spinal cord neurons in long-term culture. Exp Neurol 2008; 209:171-180
36. Das M, Rumsey J W, Bhargava N, Stancescu M, Hickman J J. A defined long-term in vitro tissue engineered model of neuromuscular junctions. Biomaterials 2010; 31:4880-4888.
37. Lochter A, Taylor J, Braunewell K H, Holm J, Schachner M. Control of neuronal morphology in vitro: interplay between adhesive substrate forces and molecular instruction. J Neurosci Res 1995; 42(2):145-158.
38. Popat K C, Sharma S, Desai T A. Quantitative XPS Analysis of PEG-Modified Silicon Surfaces. J Phys Chem B 2004; 108(17):5185-5188.
39. Popat K C, Mor G, Grimes C A, Desai T A. Surface modification of nanoporous alumina surfaces with poly (ethylene glycol). Langmuir 2004; 20(19):8035-8041.
40. Natarajan A R, Rong Q, Katchman A N, Ebert S N. Intrinsic cardiac catecholamines help maintain beating activity in neonatal rat cardiomyocyte cultures. Pediatr Res 2004; 56(3):411-417.
41. Sathaye A, Bursac N, Sheehy S, Tung L. Electrical pacing counteracts intrinsic shortening of action potential duration of neonatal rat ventricular cells in culture. J Mol Cell Cardiol 2006t; 41(4):633-641.
42. Molnar P, Kang J F, Bhargava N, Das M, Hickman J J. Synaptic connectivity in engineered neuronal networks. Methods Mol Biol 2007; 403:165-173.
43. Egert U, Banach K, Meyer T. Analysis of cardiac myocyte activity dynamics with microelectrode arrays. In: Taketani M B M, editor. Advances in network electrophysiology using multi electrode arrays: Springer, 2006. p. 274-290.
44. Spach M S. The role of cell-to-cell coupling in cardiac conduction disturbances. Adv Exp Med Biol 1983; 161:61-77.
45. Spach M S, Heidlage J F. The stochastic nature of cardiac propagation at a microscopic level. Electrical description of myocardial architecture and its application to conduction. Circ Res 1995; 76(3):366-380.
46. Halbach M, Egert U, Hescheler J, Banach K. Estimation of action potential changes from field potential recordings in multicellular mouse cardiac myocyte cultures. Cell Physiol Biochem 2003; 13(5):271-284.
47. Yeung C K, Sommerhage F, Wrobel G, Offenhausser A, Chan M, Ingebrandt S. Drug profiling using planar microelectrode arrays. Anal Bioanal Chem 2007; 387(8):2673-2680.
48. Iravanian S, Nabutovsky Y, Kong C R, Saha S, Bursac N, Tung L. Functional reentry in cultured monolayers of neonatal rat cardiac cells. Am J Physiol Heart Circ Physiol 2003; 285(1):H449-456.
49. Entcheva E K, Y. Tchernev, E. Tung, L. Fluorescence imaging of electrical activity in cardiac cells using an all-solid-state system IEEE Trans Biomed Eng 2004; 51(2):331-341.
50. Stinstra J, Roberts S, Pormann J, Macleod R, Henriquez C. A Model of 3D Propagation in Discrete Cardiac Tissue. Comput Cardiol 2006; 33:41-44.
51. Klabunde R E. Cardiovascular physiology concepts. illustrated ed: Lippincott Williams & Wilkins, 2004.
52. Inoue N, Ohkusa T, Nao T, Lee J K, Matsumoto T, Hisamatsu Y, et al. Rapid electrical stimulation of contraction modulates gap junction protein in neonatal rat cultured cardiomyocytes: Involvement of Mitogen-Activated Protein Kinases and Effects of Angiotensin II-Receptor Antagonist. J Am Coll Cardiol 2004; 44:914-922.
53. Lu H R, Vlaminckx E, Van de Water A, Rohrbacher J, Hermans A, Gallacher D J. In-vitro experimental models for the risk assessment of antibiotic-induced QT prolongation. Eur J Pharmacol 2006; 553(1-3):229-239.

That which is claimed:

1. An in vitro method of testing the effect of a compound on cardiac function, the method comprising:
 a) providing a culture of patterned spontaneously beating cardiomyocytes comprising:
  i) a support substrate bearing a multielectrode array;
  ii) a first surface resistant to cell attachment and deposited on said support substrate wherein the first surface covers the multi-electrode array;
  iii) a pattern ablated on said first surface;
  iv) a second surface that promotes cell attachment deposited on the pattern ablated on the first surface; and
  v) cardiomyocytes adherent to said second surface and growing aligned along said pattern to provide said culture of patterned spontaneously beating cardiomyocytes;
 b) recording a first electrical output from said culture of patterned spontaneously beating cardiomyocytes;
 c) contacting said culture of patterned spontaneously beating cardiomyocytes with a compound being tested;
 d) recording a second electrical output from said culture of patterned spontaneously beating cardiomyocytes after contacting with the compound; and
 e) determining a change between the first and second electrical outputs as an indicator of altered cardiac function.

2. The method of claim 1, wherein the first surface comprises a material selected from the group consisting of polyethylene glycol, polyacrylic acid and polyacrylamide.

3. The method of claim 1, wherein the material is polyethylene glycol deposited essentially as a monolayer.

4. The method of claim 1, wherein the pattern is ablated by photolithography.

5. The method of claim 1, wherein said culture of patterned spontaneously beating cardiomyocytes are of mammalian origin.

6. The method of claim 1, wherein said culture of patterned spontaneously beating cardiomyocytes are of rat origin.

7. The method of claim 1, wherein said culture of patterned spontaneously beating cardiomyocytes are derived from human embryonic stem cells.

8. The method of claim 1, wherein the second surface comprises fibronectin, trimethoxysilylpropyldiethylenetriamine, or pure glass.

* * * * *